(12) United States Patent
Evans et al.

(10) Patent No.: US 12,048,527 B2
(45) Date of Patent: Jul. 30, 2024

(54) EXHALED GAS MEASUREMENT COMPENSATION DURING HIGH FLOW RESPIRATORY THERAPY

(71) Applicant: Fisher & Paykel Healthcare Limited, Auckland (NZ)

(72) Inventors: Alicia Jerram Hunter Evans, Auckland (NZ); Callum James Thomas Spence, Auckland (NZ); Craig Karl White, Auckland (NZ); Geraldine Keogh, Auckland (NZ); Matthew Jon Payton, Auckland (NZ); Laurence Gulliver, Auckland (NZ); Milanjot Singh Assi, Auckland (NZ); Samantha Dale Oldfield, Auckland (NZ); Laith Adeeb Hermez, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1025 days.

(21) Appl. No.: 16/905,429

(22) Filed: Jun. 18, 2020

(65) Prior Publication Data
US 2020/0383606 A1 Dec. 10, 2020

Related U.S. Application Data

(63) Continuation of application No. 15/508,703, filed as application No. PCT/IB2015/056729 on Sep. 4, 2015, now Pat. No. 10,722,143.
(Continued)

(51) Int. Cl.
*A61B 5/083* (2006.01)
*A61B 5/091* (2006.01)
(Continued)

(52) U.S. Cl.
CPC ............ *A61B 5/0836* (2013.01); *A61B 5/091* (2013.01); *A61M 16/0051* (2013.01);
(Continued)

(58) Field of Classification Search
CPC ....... A61B 5/0836; A61B 5/087; A61B 5/091; A61M 16/0051; A61M 16/0069;
(Continued)

(56) References Cited

U.S. PATENT DOCUMENTS 5,307,795 A   5/1994 Whitwam et al.
6,238,351 B1  5/2001 Orr et al.
(Continued)

FOREIGN PATENT DOCUMENTS

EP        0728493 B1    3/2002
EP        2633806 A1    9/2013
WO    WO 2008/079869   7/2008

OTHER PUBLICATIONS

International Search Report and Written Opinion for PCT/IB2015/056729 dated Dec. 23, 2015 in 12 pages.
(Continued)

*Primary Examiner* — Joshua Lee
(74) *Attorney, Agent, or Firm* — Knobbe, Martens, Olson & Bear, LLP

(57) ABSTRACT

The present disclosure relates to determining a corrected exhaled gas measurement during high flow respiratory therapy. Measuring exhaled gas concentration during high flow respiratory therapy is difficult and inaccurate due to a phenomenon known as flushing. The high flows delivered to the patient flush the dead space in the conducting airways, which causes a dilution effect that results in underestimated or overestimated exhaled gas measurement depending on the gas composition delivered by the high flow system. This can lead to incorrect clinical measurements and diagnoses. Vari-
(Continued)

ous algorithms are disclosed herein to account for the dilution effect caused by flushing, allowing for the method of measuring gas concentrations to still be used accurately for clinical measurements.

20 Claims, 10 Drawing Sheets

Related U.S. Application Data

(60) Provisional application No. 62/046,052, filed on Sep. 4, 2014.

(51) Int. Cl.
  *A61M 16/00* (2006.01)
  *A61M 16/06* (2006.01)
  *A61M 16/08* (2006.01)
  *A61M 16/10* (2006.01)

(52) U.S. Cl.
  CPC .... *A61M 16/0069* (2014.02); *A61M 16/0096* (2013.01); *A61M 16/06* (2013.01); *A61M 16/085* (2014.02); *A61M 16/0883* (2014.02); *A61M 2016/0027* (2013.01); *A61M 2016/0042* (2013.01); *A61M 16/0666* (2013.01); *A61M 2016/102* (2013.01); *A61M 2205/3334* (2013.01); *A61M 2230/432* (2013.01); *A61M 2230/435* (2013.01)

(58) Field of Classification Search
  CPC .............. A61M 16/0096; A61M 16/06; A61M 16/0666; A61M 16/085; A61M 16/0883; A61M 2016/0027; A61M 2016/0042; A61M 2016/102; A61M 2205/3334; A61M 2230/432; A61M 2230/435
  See application file for complete search history.

(56) References Cited

U.S. PATENT DOCUMENTS

| | | | |
|---|---|---|---|
| 6,581,595 B1 | 6/2003 | Murdock et al. | |
| 8,021,308 B2 * | 9/2011 | Carlson ................. | A61B 5/0833 600/529 |
| 8,677,999 B2 * | 3/2014 | Allum ................... | A61M 16/20 128/204.25 |
| 9,095,276 B2 * | 8/2015 | Carlson ................. | G01N 33/004 |
| 9,936,897 B2 * | 4/2018 | Carlson ................. | A61B 5/0836 |
| 10,034,621 B2 * | 7/2018 | Wondka ................ | A61B 5/0836 |
| 10,722,143 B2 | 7/2020 | Evans et al. | |
| 2002/0053346 A1 * | 5/2002 | Curti .................... | A61M 16/085 128/207.18 |
| 2002/0055685 A1 | 5/2002 | Levitsky et al. | |
| 2003/0208133 A1 * | 11/2003 | Mault ................... | G01N 33/497 600/531 |
| 2006/0201503 A1 | 9/2006 | Breen | |
| 2008/0228096 A1 * | 9/2008 | Jaffe .................... | A61M 16/026 600/532 |
| 2009/0118633 A1 * | 5/2009 | Jaffe .................... | A61B 5/0836 600/532 |
| 2009/0120435 A1 | 5/2009 | Slessarev et al. | |
| 2010/0071693 A1 * | 3/2010 | Allum ................ | A61M 16/0833 128/205.24 |
| 2011/0009763 A1 * | 1/2011 | Levitsky ........... | A61M 16/1005 128/207.18 |
| 2011/0253136 A1 * | 10/2011 | Sweeney ........... | A61M 16/0069 128/207.18 |
| 2012/0234324 A1 | 9/2012 | Orr | |
| 2012/0310104 A1 * | 12/2012 | Van Kesteren ........ | A61B 5/082 600/532 |
| 2013/0165806 A1 * | 6/2013 | Wondka ............... | A61B 5/0836 600/532 |
| 2014/0276169 A1 | 9/2014 | Chua | |
| 2015/0230731 A1 | 8/2015 | Levitsky et al. | |
| 2018/0207386 A1 * | 7/2018 | Kertser ............. | A61M 16/0833 |

OTHER PUBLICATIONS

Supplementary European Search Report and Written Opinion for PCT/IB2015056729 mailed Mar. 18, 2018 in 6 pages.

* cited by examiner

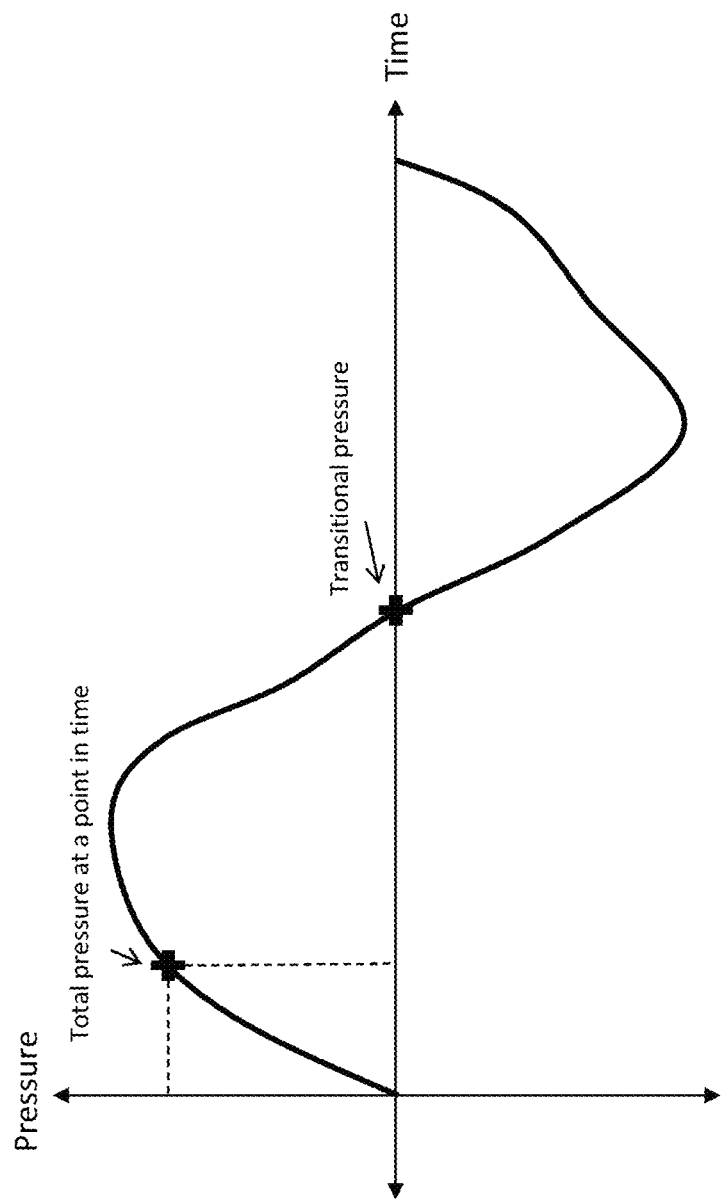

EXHALED GAS MEASUREMENT COMPENSATION DURING HIGH FLOW RESPIRATORY THERAPY

INCORPORATION BY REFERENCE TO ANY PRIORITY APPLICATIONS

This application is a continuation of U.S. application Ser. No. 15/508,703, filed Mar. 3, 2017, titled "EXHALED GAS MEASUREMENT COMPENSATION DURING HIGH FLOW RESPIRATORY THERAPY," now U.S. Pat. No. 10,722,143, which is a national phase entry of PCT Application No. PCT/IB2015/056729, filed Sep. 4, 2015, titled "EXHALED GAS MEASUREMENT COMPENSATION DURING HIGH FLOW RESPIRATORY THERAPY," which is claims the priority benefit of U.S. Provisional Application No. 62/046,052, filed Sep. 4, 2014, the entirety of which is hereby incorporated by reference herein. Any and all applications for which a foreign or domestic priority claim is identified in the Application Data Sheet as filed with the present application are hereby incorporated by reference under 37 CFR 1.57.

In addition, the applications listed on the following chart are specifically incorporated herein in their entireties by reference.

| Filing Date | Title | application Ser. No. |
| --- | --- | --- |
| Sep. 4, 2013 | MECHANISM PRIORITISATION | 61/873,710 |
| Feb. 26, 2014 | METHOD AND APPARATUS FOR FLOW THERAPY BREATHING APPARATUS | 61/944,800 |
| Oct. 4, 2013 | FLOW DELIVERY SYSTEM | 61/886,921 |
| Dec. 2, 2013 | METHODS AND APPARATUS FOR FLOW THERAPY BREATHING APPARATUS | 61/910,812 |
| Nov. 19, 2013 | HIGH FLOW OSCILLATORY VENTILATION MECHANISM | 61/906,328 |
| Dec. 19, 2013 | FLOW AND/OR PRESSURE OSCILLATION | 61/918,620 |
| May 16, 2014 | METHODS AND APPARATUS FOR FLOW THERAPY | 61/994,374 |
| Jun. 12, 2014 | METHODS AND APPARATUS FOR FLOW THERAPY | 62/011,221 |
| Aug. 13, 2014 | METHODS AND APPARATUS FOR FLOW THERAPY | 62/036,769 |
| Sep. 4, 2014 | METHODS AND APPARATUS FOR FLOW THERAPY | 62/046,000 |
| Mar. 31, 2015 | METHODS, APPARATUS AND SYSTEMS FOR PRE-OXYGENATION THERAPY | 62/140,592 |
| Mar. 31, 2015 | FLOW THERAPY SYSTEM AND METHOD | 62/140,633 |

FIELD OF DISCLOSURE

The present disclosure relates to the field of respiratory therapy and related physiological measurements.

BACKGROUND OF THE INVENTION

Monitoring respiratory function plays an important role in the management of patients in clinical settings. A change to respiratory gas composition is one aspect of respiratory function that can be used to assess patient health and respiratory status. The concentrations of gases in a patient's respiratory system are the result of ventilation, gas exchange, gas transport, and the control of ventilation (internal or external). Some examples of respiratory gases monitored include oxygen ($O_2$), carbon dioxide ($CO_2$), nitrous oxide ($N_2O$), and nitrogen ($N_2$).

For example, the concentration of $CO_2$ expelled from the lungs during expiration may be the result of ventilation, perfusion, metabolism, and their interactions. Changes in $CO_2$ concentration reflect changes in any or all of these factors. It is therefore vital to monitor and measure the concentration of $CO_2$ to provide a snapshot of a patient's respiratory status. It provides immediate information on $CO_2$ production, ventilation perfusion (V/Q) status, and elimination of $CO_2$ from the lungs.

Capnography is the measurement of exhaled $CO_2$. This is the $CO_2$ that has diffused out of the blood into the alveolar air and is subsequently exhaled. End tidal $CO_2$ ($ETCO_2$) is the partial pressure or maximal concentration of $CO_2$ at the end of an exhaled breath and is an important metric used to non-invasively estimate the patient's arterial $CO_2$ concentration ($PaCO_2$). The difference between $ETCO_2$ and $PaCO_2$ is usually between 2 and 5 mmHg. Therefore, $ETCO_2$ is a good representation of $PaCO_2$. However, any conditions causing ventilation perfusion mismatch will cause $ETCO_2$ to underestimate $PaCO_2$.

SUMMARY OF THE DISCLOSURE

When gas measurements, such as capnography, are used in conjunction with non-sealed respiratory flow systems, assessments of patient condition are difficult to conduct due to the flushing mechanism of the flow therapy. Non-sealed respiratory flow/pressure systems can include, for example, high flow respiratory therapy (including, for example, nasal high flow therapy), low flow therapy, or other flow/pressure therapies applied to the mouth and/or nares. High flow therapy typically includes, but is not limited to, flows of 10-100 L/min. Low flow therapy typically includes, but is not limited to, flows of 0-10 L/min.

The flows delivered to the patient flush the dead space in the upper airways resulting in a non-uniform distribution of gas from the alveoli to the nose and mouth. For example, alveolar $CO_2$ is mixed with fresh gas delivered via the cannula, causing a dilution of exhaled $CO_2$ that is sampled and measured. This can lead to an incorrect diagnosis or assumptions about disease conditions. The $ETCO_2$, or any other measurement of exhaled gases, measured during high flow therapy tends to incorrectly estimate the concentration, and this incorrect estimation increases in magnitude with increasing flow rate. For example, a healthy individual who receives high flow respiratory therapy at 30 L/min can have reported $ETCO_2$ that is 50% lower, and more preferably lower than 80%, of its actual value, resulting in inaccurate assessments. The same is true for any other non-sealed respiratory flow therapies where gas is allowed to escape making measurements of exhaled gas difficult.

The present disclosure provides systems and methods for compensating gas measurements for this dilution error caused by respiratory flow therapy allowing gas measurement techniques to be used during respiratory flow therapy. Although disclosed mainly with respect to high flow respiratory therapy and exhaled $CO_2$ measurements, the systems and methods disclosed herein are equally applicable to any other exhaled gas measurements, including, but not limited to $O_2$, $N_2$, nitrous oxide, and volatiles (for example, anesthetic gas) measurements, obtained during any type of non-sealed respiratory flow therapy, and should not be limited to exhaled $CO_2$ measurements solely during high flow respiratory therapy.

In one aspect there is a system for estimating exhaled gas during flow respiratory therapy, the system comprising: a respiratory flow therapy system; an exhaled gas monitoring system; and a processing arrangement which receives exhaled gas measurement data from the exhaled gas monitoring system and flow data from the respiratory flow therapy system and determines a compensated exhaled gas measurement.

In one embodiment the flow respiratory therapy system is a high flow respiratory therapy system, and wherein the flow respiratory therapy system comprises an unsealed patient interface such that the flow respiratory therapy system is a non-sealed flow respiratory therapy system.

In one embodiment the exhaled gas is CO2

In one embodiment the exhaled CO2 monitoring system is a capnograph.

In one embodiment the exhaled CO2 monitoring system is a capnometer.

In one embodiment the non-sealed high flow respiratory therapy system is a nasal high flow respiratory system and wherein the system comprises a display arranged to display the compensated exhaled gas measurement.

In one embodiment the processing arrangement determines the compensated exhaled gas by estimating flow rate dilution.

In one embodiment the processing arrangement determines the compensated exhaled gas by estimating expiratory volume dilution.

In another aspect there is a method for estimating exhaled gas during flow respiratory therapy, the method comprising: receiving an exhaled gas measurement; receiving flow data; and determining a compensated exhaled gas measurement using a processing arrangement based on the exhaled gas measurement and the flow data.

In one embodiment the flow respiratory therapy is a non-sealed high flow respiratory therapy that involves an unsealed patient interface.

In one embodiment receiving the exhaled gas measurement comprises receiving an exhaled gas measurement from a capnograph.

In one embodiment receiving the exhaled gas measurement comprises receiving an exhaled gas measurement from a capnometer.

In one embodiment the high flow respiratory therapy is nasal high flow respiratory therapy.

In one embodiment determining the compensated exhaled gas measurement comprises determining an estimate of flow rate dilution.

In one embodiment determining the compensated exhaled gas measurement comprises determining an estimate of expiratory volume dilution.

In another aspect there is a system for estimating exhaled gas during flow respiratory therapy, the system comprising: a first sensor configured to measure a concentration of a gas of interest in a total expiratory flow, and one or more hardware computer processors in communication with the first sensor and configured to execute a plurality of computer executable instructions for: determining an exhaled concentration of the gas of interest using a patient-only contribution to an expiratory flow rate attributable to the gas of interest and an instantaneous expiratory flow rate of a patient; and displaying for diagnostic purposes the exhaled concentration of the gas of interest.

In one embodiment the first sensor is a capnometer;

In one embodiment the system further comprises a second sensor configured to measure an instantaneous expiratory flow rate of a patient, and wherein the one or more hardware computer processors are also in communication with the second sensor, and wherein the one or more hardware computer processors are further configured to execute a plurality of computer executable instructions for: determining the instantaneous expiratory flow rate of the patient, wherein the instantaneous expiratory flow rate comprises a rate of flow of gas exhaled by the patient; determining a delivered flow rate, wherein the delivered flow rate comprises a rate of flow of gas within a cannula; and determining a total expiratory flow rate using the instantaneous expiratory flow rate and the delivered flow rate, wherein the total expiratory flow rate comprises the rate of flow of gas associated with a total expiratory flow.

In one embodiment the one or more hardware computer processors are further configured to execute a plurality of computer executable instructions for: determining the concentration of the gas of interest in the total expiratory flow; determining a portion of the total expiratory flow rate attributable to the gas of interest using the total expiratory flow rate and the concentration of the gas of interest in the total expiratory flow; determining a concentration of the gas of interest within the cannula; and determining a portion of the delivered flow rate attributable to the gas of interest using the delivered flow rate and the concentration of the gas of interest within the cannula.

In one embodiment the one or more hardware computer processors are further configured to execute a plurality of computer executable instructions for: determining a patient-only contribution to the expiratory flow rate attributable to the gas of interest using the portion of the total expiratory flow rate attributable to the gas of interest and the portion of the delivered flow rate attributable to the gas of interest.

In one embodiment the flow respiratory therapy is a non-sealed high flow respiratory therapy, and wherein the system further comprises an unsealed patient interface.

In one embodiment the gas of interest is CO2 and wherein the first sensor is a capnometer.

In one embodiment determining a portion of the total expiratory flow rate attributable to the gas of interest involves multiplying the total expiratory flow rate by the concentration of the gas of interest in the total expiratory flow.

In one embodiment determining a portion of the delivered flow rate attributable to the gas of interest involves multiplying the delivered flow rate and the concentration of the gas of interest within the cannula.

In one embodiment determining a patient-only contribution to the expiratory flow rate attributable to the gas of interest involves subtracting the portion of the delivered flow rate attributable to the gas of interest from the portion of the total expiratory flow rate attributable to the gas of interest.

In one embodiment determining a concentration of a gas of interest in the total expiratory flow involves using measurements from the first sensor.

In another aspect there is a system for estimating exhaled gas during flow respiratory therapy, the system comprising: a first sensor configured to measure a concentration of a gas of interest in a total expiratory flow, and one or more hardware computer processors in communication with the first sensor and the second sensor and configured to execute a plurality of computer executable instructions for: determining an exhaled concentration of the gas of interest using a patient-only contribution to a diluted expired volume of the gas of interest and a patient expiratory volume over a time of interest; and displaying for diagnostic purposes the exhaled concentration of the gas of interest.

In one embodiment the first sensor is a capnometer;

In one embodiment the system further comprises a second sensor configured to measure an expiratory flow rate of a patient, and wherein the one or more hardware computer processors are also in communication with the second sensor, and wherein the one or more hardware computer processors are further configured to execute a plurality of computer executable instructions which cause the one or more hardware computer processors to: determine the expiratory flow rate of the patient, wherein the expiratory flow rate comprises a rate of flow of gas exhaled by the patient in a expiratory breath; determine an expiratory time, wherein the expiratory time comprises the duration of the expiratory breath; and generate a model of the expiratory breath using the expiratory flow rate and the expiratory time.

In one embodiment the one or more hardware computer processors are further configured to execute a plurality of computer executable instructions which cause the one or more hardware computer processors to: determine a time of interest, wherein the time of interest is a time interval of the duration of the expiratory breath; determine a patient expiratory volume over the time of interest using the model of the expiratory breath, wherein the patient expiratory volume comprises a volume of gas exhaled by the patient during the expiratory breath; and determine a volume of gas delivered from a cannula over the time of interest, wherein the volume of gas delivered from the cannula over the time of interest is associated with a delivered flow rate, and wherein the delivered flow rate comprises a rate of flow of gas within the cannula.

In one embodiment the one or more hardware computer processors are further configured to execute a plurality of computer executable instructions which cause the one or more hardware computer processors to: determining a total volume of gas expired over the time of interest using the patient expiratory volume over the time of interest and the volume of gas delivered from the cannula over the time of interest; determining a concentration of a gas of interest for a total expiration, wherein the total expiration is associated with the total volume of gas expired over the time of interest; and determining a diluted expired volume of the gas of interest using the total volume of gas expired over the time of interest and the concentration of the gas of interest for the total expiration.

In one embodiment the one or more hardware computer processors are further configured to execute a plurality of computer executable instructions which cause the one or more hardware computer processors to: determine a concentration of the gas of interest delivered from the cannula; determine a volume of the gas of interest delivered from the cannula over the time of interest by using the volume of gas delivered from the cannula over the time of interest and the concentration of the gas of interest delivered from the cannula; and determine a patient-only contribution to the diluted expired volume of the gas of interest.

In one embodiment the gas of interest is CO2 and wherein the first sensor is a capnometer.

In one embodiment calculating a total volume of gas expired over the time of interest involves adding the patient expiratory volume over the time of interest to the volume of gas delivered from the cannula over the time of interest;

In one embodiment determining a concentration of the gas of interest within the total volume of gas expired over the time of interest involves using measurements from the first sensor.

In another aspect there is a system for estimating exhaled gas during flow respiratory therapy, the system comprising: a first sensor configured to measure a concentration of a gas of interest in a total expiratory flow, wherein the first sensor is a capnometer; and one or more hardware computer processors in communication with the first sensor and the second sensor and configured to execute a plurality of computer executable instructions for: determining an exhaled concentration of the gas of interest using a patient-only contribution to a diluted expired volume of the gas of interest and a patient expiratory volume over a time interval; and displaying for diagnostic purposes the exhaled concentration of the gas of interest.

In one embodiment the system further comprises a second sensor configured to measure an expiratory flow rate of a patient, and wherein the one or more hardware computer processors are also in communication with the second sensor, and wherein the one or more hardware computer processors are further configured to execute a plurality of computer executable instructions for: determining a first expiratory flow rate of the patient, wherein the first expiratory flow rate comprises a rate of flow of gas exhaled by the patient in a expiratory breath at a first time; determining a second expiratory flow rate of the patient, wherein the second expiratory flow rate comprises a rate of flow of gas exhaled by the patient in the expiratory breath at a second time; and determining a patient expiratory volume over a time interval using the first expiratory flow rate and the second expiratory flow rate, wherein the time interval is a duration of time between the first time and the second time, and wherein the time interval is configured to be a short time interval.

In one embodiment the one or more hardware computer processors are further configured to execute a plurality of computer executable instructions for: determining a delivered flow rate over the time interval, wherein the delivered flow rate is associated with the rate of flow of gas within a cannula; determining a volume of gas delivered by the cannula over the time interval using the delivered flow rate of the time interval; and determining a total volume of gas expired over the time interval, wherein the total volume expired over the time interval is calculated by adding the patient expiratory volume over the time interval to the volume of gas delivered by the cannula over the time interval.

In one embodiment the one or more hardware computer processors are further configured to execute a plurality of computer executable instructions for: determining a concentration of a gas of interest in the total volume of gas expired over the time interval; determining a diluted expired volume of the gas of interest by multiplying the total volume of gas expired over the time interval with the concentration of the gas of the interest in the total volume of gas expired over the time interval; and determining a concentration of the gas of interest delivered from the cannula.

In one embodiment the one or more hardware computer processors are further configured to execute a plurality of computer executable instructions for: determining a volume of the gas of interest delivered from the cannula over the time interval by multiplying the volume of gas delivered from the cannula over the time interval with the concentration of the gas of interest delivered from the cannula; and determining a patient-only contribution to the diluted expired volume of gas of interest by subtracting the volume of the gas of interest delivered from the cannula over the time interval from the diluted expired volume of the gas of interest.

In one embodiment the gas of interest is CO2 and wherein the first sensor is a capnometer.

In one embodiment calculating a patient expiratory volume involves trapezoidal approximation of the first expiratory flow rate and the second expiratory flow rate over the time interval.

In another aspect there is a system for estimating exhaled gas during flow respiratory therapy, the system comprising: a first sensor configured to measure a concentration of a gas of interest in a total expiratory flow; and one or more hardware computer processors in communication with the first sensor and the second sensor and configured to execute a plurality of computer executable instructions for: determining an exhaled concentration of the gas of interest by dividing a pressure contribution of the gas of interest in an expiratory pressure by the expiratory pressure; and displaying for diagnostic purposes the exhaled concentration of the gas of interest.

In one embodiment the system further comprises a second sensor configured to measure an expiratory pressure of a patient, and wherein the one or more hardware computer processors are also in communication with the second sensor, and wherein the one or more hardware computer processors are further configured to execute a plurality of computer executable instructions for: determining a pressure associated with a resistance to flow; determining a transitional pressure of a patient; and determining the expiratory pressure of the patient over a breathing cycle of the patient using the second sensor.

In one embodiment the one or more hardware computer processors are further configured to execute a plurality of computer executable instructions for: determining an expiratory pressure using the transitional pressure and the expiratory pressure; determining a pressure associated with a cannula flow using the pressure associated with the resistance to flow and the transitional pressure; and determining a pressure contribution of a gas of interest in the cannula flow by multiplying a concentration of the gas of interest in the cannula flow with the pressure associated with the cannula flow.

In one embodiment the first sensor is a capnometer and wherein the one or more hardware computer processors are further configured to execute a plurality of computer executable instructions for: determining a pressure contribution of the gas of interest in the total expiratory pressure by multiplying the total expiratory pressure by a concentration of the gas of interest in the total expiratory pressure; and determining a pressure contribution of the gas of interest in the expiratory pressure from the patient using the pressure contribution of the gas of interest in total expiratory pressure and the pressure from the cannula flow.

BRIEF DESCRIPTION OF THE DRAWINGS

FIG. 10 illustrates how transitional pressure can be determined from a pressure waveform of a breathing cycle.

DETAILED DESCRIPTION

Figure 1:
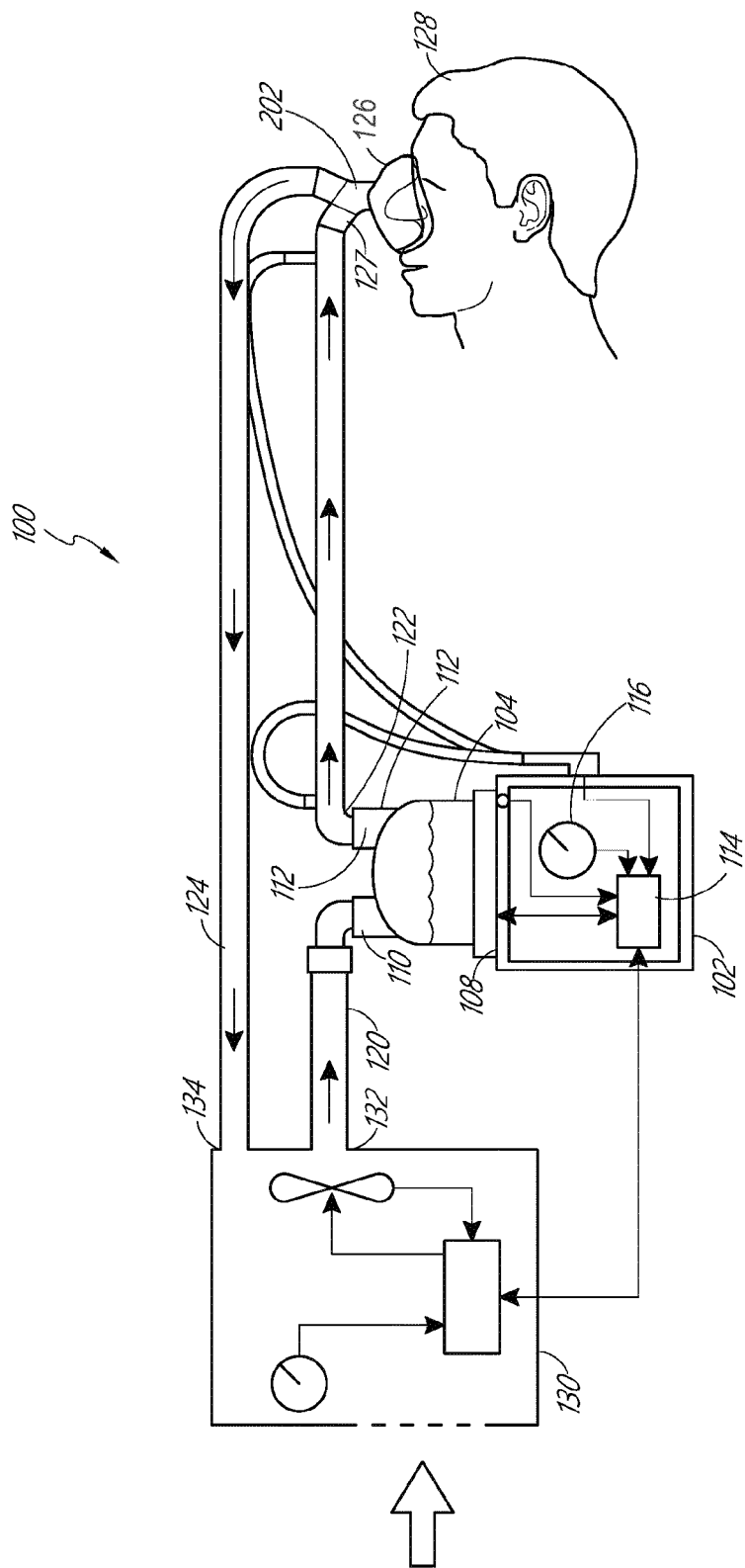
FIG. 1 illustrates an example embodiment of a humidification system.

Although certain embodiments and examples are described below, those of skill in the art will appreciate that the disclosure extends beyond the specifically disclosed embodiments and/or uses and obvious modifications and equivalents thereof. Thus, it is intended that the scope of the present disclosure should not be limited by any particular embodiments described below.

In some configurations, the gas supply is configured to supply gas to the humidifier at a flow rate between about 5 liters per minute and about 120 liters per minute.

As relatively high gas delivery flow rates may be used with the embodiments or configurations described herein, the gases being supplied or delivered to the user or patient can may be delivered to different parts of the user's or a patient's airway. The gases being supplied may reach the patient's lungs or any part of the respiratory system.

For example, according to those various embodiments and configurations described herein, a flow rate of gases supplied or provided to an interface or via a system, such as through a flow path, may comprise, but is not limited to, flows of at least about 5, 10, 20, 30, 40, 50, 60, 70, 80, 90 or 100 L/min, or more, and useful ranges may be selected between any of these values (for example, about 40 to about 80, about 50 to about 80, about 60 to about 80, about 70 to about 80, about 80 l/min). Optionally, the gases supplied may be delivered in a fully saturated or humidified condition, or a saturated or humidified gas may be blended with other gases for supply or delivery to a patient interface or the patient.

Low flow therapy can be between 0.1 L to 5 L per minute. The invention is particularly suitable for high flow therapy but can be used with low flow therapy.

Measuring exhaled gas concentration is a quantitative, non-invasive, simple and safe method that can be used for a variety of gases and for a variety of purposes. For example, it may be used in conjunction with low flow therapy or high flow therapy. As another example, measuring exhaled $CO_2$ can be used to infer a patient's arterial $CO_2$ concentration and/or ventilation perfusion (V/Q) status. Measuring exhaled nitric oxide can be used to measure airway inflammation. The measurement can also be used for continuous monitoring which is unavailable with other methods such as arterial blood gas samples.

However, measuring exhaled gas concentration when high flow is applied is difficult and inaccurate. This is because of flushing, one of the mechanisms unique to high flow. Flushing is a mechanism in which the flows delivered to the patient "flush" the dead space in the conducting airways. The result of flushing is a non-uniform distribution of gas from the lungs to the nose and mouth. Breathing without high flow involves gas from the lungs entering into the nasal cavity and being expelled out into the atmosphere.

However, breathing with nasal high flow shows gas from the high flow interface changing the gas composition in the nasal cavity and altering the gas concentration that would normally be measured when high flow is not applied. Flushing causes a dilution effect, underestimating or overestimating the exhaled gas measurement depending on the gas composition delivered by the high flow system. This can lead to incorrect clinical measurements and diagnoses. A technique and system to account for the dilution effect caused by flushing is needed to allow for measurement of gas concentrations to still be used accurately for clinical measurements.

The present disclosure provides systems and techniques for compensating gas measurements for this dilution error caused by respiratory flow therapy allowing gas measurement techniques to be used during respiratory flow therapy. The gas measured may be an exhaled gas, such that the current techniques described can be used to determine measurements for $CO_2$, O2, N2, nitrous oxide, volatiles (i.e., anesthetic gases), or any other exhaled gases.

The term exhaled gases includes any gases that are evacuated, or come, from the airways or lungs of the patient. The term exhaled covers both active exhalation by a human (for example, using the diaphragm and/or chest muscles) as well as removal of gases when a person is apneic (not spontaneously breathing). There are mechanisms that can cause gases from the lungs and airways to exit, and the term exhaled in this disclosure is broad enough to be applied to a person that is not spontaneously breathing.

The present disclosure specifically pertains to determining the value, amount, and/or concentration of exhaled gases. Examples of this include flow dilution, volume dilution, and pressure dilution techniques. These techniques account for the dilution and flushing caused by applying respiratory flow therapy, particularly high flow therapy. The high flow delivered to the nose causes dilution of gases coming out of the mouth because much of the high flow from a gas therapy device exits out of the mouth rather than reaching down into the lungs. The amount of gases leaving the mouth does not equal the exhaled gases from the patient, which the disclosed techniques compensate for.

The currently disclosed techniques and systems are advantageous because they may function as non-invasive monitoring techniques of a patient's respiration. They do not require invasive scopes or sensors, as the amount of exhaled gases above a certain threshold may signify the patient is breathing. The current disclosure may also serve as non-invasive techniques of identifying if a patient has a patent (unblocked airway). If there are gases coming out of the lungs and airways then the airways are not blocked. The capability of making this observation reduces the need for more invasive monitoring technology. Thus, the present disclosure serves to further the non-invasive benefits of measuring exhaled gas concentration.

The term expiratory refers to gases exhaled from the patient.

The term end tidal $CO_2$ ($ETCO_2$) refers to the measurement, level, amount, or concentration of carbon dioxide released during an exhaled breath (expiration) of the patient.

The term $PaCO_2$ refers to the partial pressure of arterial carbon dioxide. It may be a measurement, level, amount, or concentration of carbon dioxide in the blood of the patient.

The term cannula flow rate refers to the delivered flow rate from the cannula once the cannula is on the patient, or when the cannula is engaged with the patient's nares. It may also be referred to as delivered flow rate.

The term processor may refer to an integrated circuit, microprocessor, controller, external processor, or a computer, such as a laptop, or PC. Alternatively, the processor may be a remote processor or mobile processing device such as a server, tablet, or mobile device, such that processing is performed by the processor communicating with the sensor using a suitable wired or wireless protocol.

Figure 2:
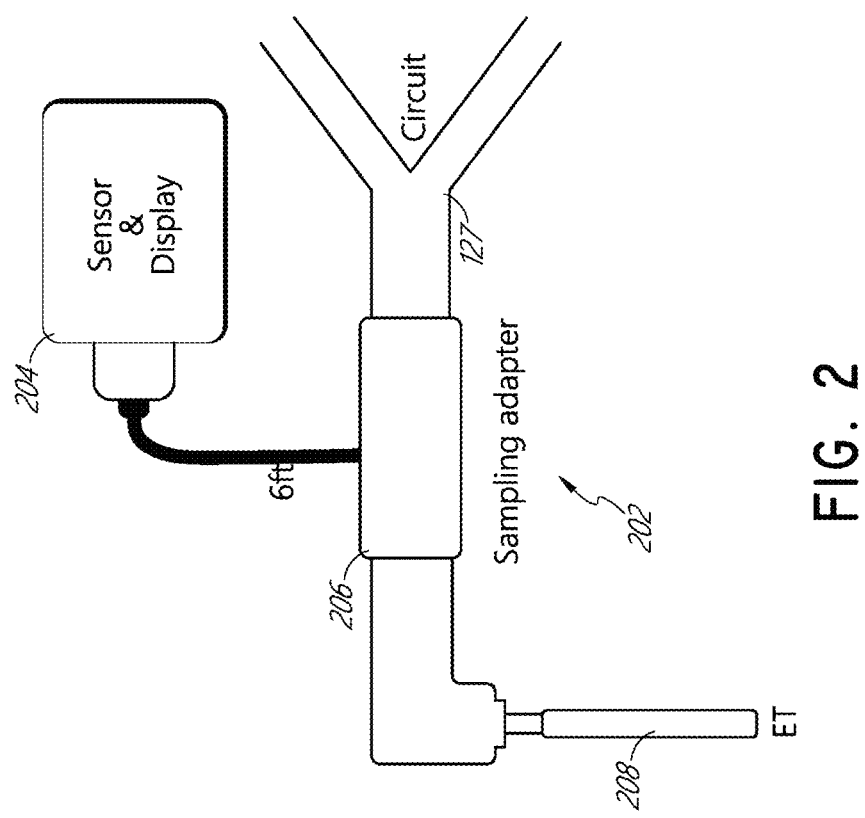
FIG. 2 illustrates an example capnography sensor in an embodiment of a flow therapy system.

General Flow Therapy System (FIGS. 1 and 2)

FIG. 1 illustrates an example embodiment of a flow therapy system, such as high flow therapy system 100. High flow therapy system 100 may include a heater base 102, a humidification chamber 104 (optional), and a breathing circuit or breathing circuit assembly, in which the breathing circuit assembly may include a supply conduit 120, an inspiratory conduit 122, and an expiratory conduit 124 (optional). In embodiments not shown, humidification chamber 104 and/or expiratory conduit 124 may not be present. In some embodiments, the high flow therapy system 100 further includes a gases supply 130, for example, a blower or a motor and impeller arrangement capable of providing pressurized gases suitable for breathing or use in medical procedures. Optionally, a ventilator may be utilized as a suitable source of pressurized gases. A ventilator may be a more complex respiratory apparatus that blows air based on the respiratory rate, or a set respiratory rate. In contrast, a blower may be simpler in terms of hardware or controller. The heater base 102 can include a heater plate 108. In addition, the heater base 102 can include one or more processors 114, and one or more memories or other suitable storage components. In some embodiments, the heater base 102 also have a display 116 that can provide information to and/or receive input from an operator.

In some configurations, the display 116 can have a schematic to facilitate the operator making the desired connections, in some instances in a desired order. For example, the display 116 can have a static image with lights (e.g., LED) under different regions that light in a sequence to encourage the desired connection order. In some configurations, the image can be formed on membranes that are back-screen printed behind a polyester or polycarbonate film with LEDs attached to or positioned adjacent to the film. In some configurations, the lights may begin the sequence when a switch is operated by insertion of a humidification chamber into the heater base or the like. Such configurations resolve any need for an operator to turn on the heater base to get the feedback on proper connection sequence. Other suitable arrangements also can be used.

Although the illustrated embodiment shows a humidification chamber 104, this humidification chamber 104 is optional. If humidification chamber 104 is present in the flow therapy system, then humidification chamber 104 generally includes an inlet 110 and an outlet 112 and is configured to be installed on the heater plate 108 of the heater base 102. The humidification chamber 104 is further configured to hold a volume of a liquid, such as water. The chamber 104 can include an opening or port for the connection of a liquid conduit.

The heater plate 108 heats the chamber 104 and causes at least some of the chamber 104 contents to evaporate. In some embodiments, the humidification chamber 104 can include features to help reduce the likelihood of the level of liquid in the chamber 104 from exceeding a particular level. For example, the chamber 104 can include one or more floats that rise and fall with the level of liquid in the chamber 104. When the liquid level reaches a certain level, the floats obstruct or block the port that is connected to the liquid conduit 118 to stop or slow further ingress of liquid into the chamber 104. Other similar features also can be used. In a preferred embodiment, a plurality of floats are used, each float adapted to stop the further ingress of liquid into the chamber 104. To this end, a second float provides a backup or safety mechanism, thereby further reducing the likelihood of the chamber 104 overfilling.

With reference again to FIG. 1, the breathing circuit assembly can include a supply conduit 120, an inspiratory conduit 122, and, in some configurations, an expiratory conduit 124. A gases supply end of the supply conduit 120 is configured to connect to an output 132 of the gases supply 130 and a chamber end of the supply conduit 120 is configured to connect to the chamber inlet 110 of the chamber 104. A chamber end of the inspiratory conduit 122 is configured to connect to the chamber outlet 112 of the chamber 104, and a user end of the inspiratory conduit 122 is configured to connect to the user 128 via an interface 126, for example. Interface 126 may be an unsealed nasal interface, such that the breathing circuit is not a sealed system. For example, interface 126 may include a nasal cannula including a pair of nasal prongs that engage in an unsealed-manner with the nares of the user/patient. In some configurations, interface 126 may be an endotracheal tube (ET) to supply high flow further below into the airways. Interface 126 may include a headgear or a bifurcated headgear. This disclosure is defined with respect to interface 126 having an unsealed nasal cannula that includes a pair of prongs that engage the nares of the user/patient. However, the techniques described in this disclosure may be used with any kind of patient interface. Examples of such patient interfaces include, but are not limited to: sealed masks, unsealed masks, controlled leak masks, nasal pillows, full face masks, endotracheal tubes, laryngeal masks, and so forth. In alternative embodiments the techniques described in this disclosure can be used with sealed patient interfaces such as sealed nasal masks, sealed nasal pillows or sealed full face masks.

A completely optional expiratory conduit 124 may be utilized. In embodiments that include expiratory conduit 124, a user end of the expiratory conduit 124 is configured to connect to the interface 126, and a gases supply end of the expiratory conduit 124 is configured to connect to a return 134 of the gases supply 130. In some embodiments, the user ends of the inspiratory conduit 122 and expiratory conduit 124 may optionally be connected to the interface 126 via a Y-piece 127, for example but without limitation. The Y-piece 127 is optional and typically used with a ventilator that provides breathing assistance for the user/patient. Thus, the inclusion in the flow therapy system of an expiratory conduit 124, Y-piece 127, and/or a ventilator (such as for gases supply 130) is completely optional, and these components may be individually utilized in special cases. There may be a capnography sensor or device located at, or attached at, position 202 between the interface 126 and the Y-piece 127. An example of one embodiment of such a capnography sensor is shown in FIG. 2 and discussed below. Further discussion of capnography or capnometer usage is provided in connection with FIG. 3 below.

In use, gases flow from the gases supply 130 through the supply conduit 120 and into the chamber 104 via the inlet 110. The gases are humidified within the chamber 104 and exit the chamber 104 through the outlet 112. The user inhales humidified gases supplied through the inspiratory conduit 122. The user may exhale into the atmosphere, or alternatively, the user may exhale into an expiratory conduit such as expiratory conduit 124. The inspiratory conduit 122 and/or expiratory conduit 124 can include a heating element, for example, a heating wire, to help maintain the gases at a desired temperature and to reduce the likelihood of significant condensation formation in the conduits.

Before use, an operator, such as medical personnel, must correctly connect the various components to set up the system 100. Because of the variety of components and number of connections that must be made, set-up of the system 100 can be a complex process that requires special training to complete properly. The high flow therapy system 100 can include various features as described herein to simplify the set-up process and reduce the likelihood of an incorrect set-up. In some instances, portions/elements of the system may come pre-assembled or pre-configured in order to reduce the overall assembly time.

FIG. 2 illustrates an example capnography sensor in an embodiment of a flow therapy system.

Y-Piece 127 may be the same Y-Piece 127 as in the flow therapy system shown in FIG. 1, and it may connect the inspiratory conduit and the expiratory conduit to the interface 126 of FIG. 1. Alternatively, Y-Piece 127 may connect the breathing circuit to an endotracheal tube 208 as shown here in FIG. 2. In some embodiments applicable to all embodiments described herein, there is no exhalation circuit and the expired air is discharged to the ambient air. In such configurations, the present Y-Piece 127 can be adapted to measure $CO_2$ and still discharge the expired air to the ambient air. In alternative embodiments without Y-Piece 127, the capnograph or other sensing arrangement may be located adjacent to the patient interface. In some embodiments, the measurement may be performed using a sampling cannula.

If the Y-Piece 127 is utilized, then at position 202, located between the Y-Piece 127 and the endotracheal tube 208 (or interface 126), may be a capnography sensor or similar device that may be useful in monitoring respiratory function. Alternatively, position 202 may be located between the patient interface and the inspiratory conduit, such as if Y-Piece 127 is not present. The inspiratory conduit may be connected to a patient end tube. The patient end tube may be a small section of tubing between the interface and the large inspiratory conduit. The inspiratory conduit may connect to the patient end conduit via a coupler. There may be a sampling adapter 206 that measures the concentration of a respiratory gas at position 202, and the sampling adapter 206 may be connected to the actual sensor 204. Sampling adaptor 206 and the sensor 204 may be part of a sensing arrangement. The sensing arrangement may alternatively just include sensor 204. Sensor 204 may also include a display that provides at least the information about the concentration of the respiratory gas. In some embodiments, the sensor 204 and/or attached display may take the place of sampling adapter 206 in order to directly monitor the gas that passes between Y-Piece 127 and endotracheal tube 208, or alternatively the endotracheal tube may be substituted for a nasal cannula or other interface suitable with high flow therapy. When position 202 is located between the patient interface and the inspiratory conduit (such as when optional Y-piece 127 is not used), then the sensing arrangement may alternatively be positioned at the coupler, be part of the coupler, or be adjacent to the coupler. Alternatively, the sensing arrangement may be position at the patient interface or adjacent to the interface.

Figure 3:
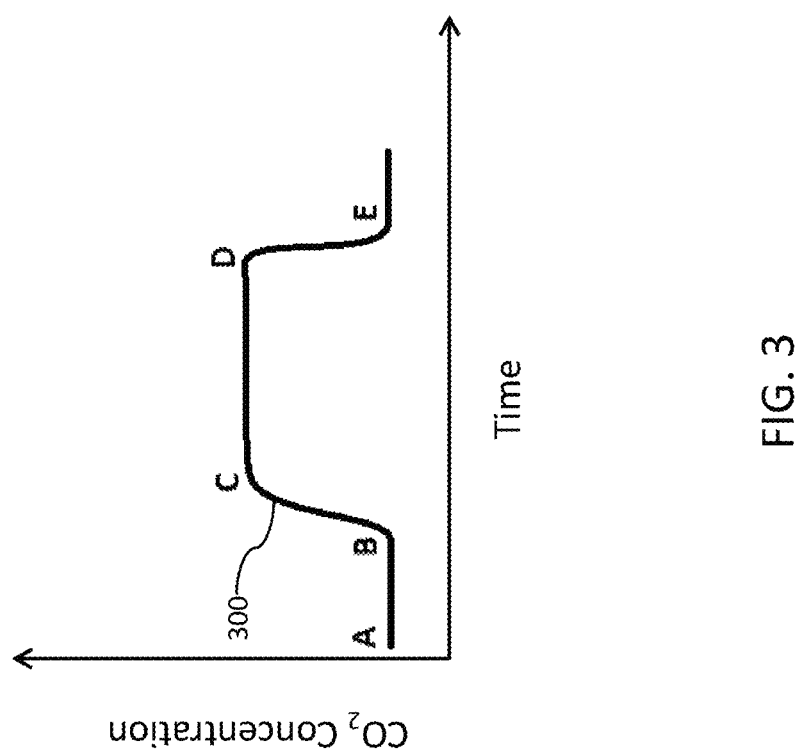
FIG. 3 illustrates an example capnogram waveform showing the amount of exhaled $CO_2$ present during a typical breath cycle.

Capnogram Analysis (FIG. 3)

Exhaled gas measurements have a number of important uses. For example, exhaled $CO_2$ measurements assist in confirming correct intubation, assist in continuous monitoring of endotracheal tube placement during patient transport and assist in assessing ventilation status. Typically, exhaled CO₂ is monitored with either a capnometer or capnograph. A capnometer measures and displays the concentration of end tidal $CO_2$ as a percentage and/or partial pressure. A capnograph has the same functionality as a capnometer but also includes a calibrated, visual waveform recording of the concentrations of inspired and exhaled $CO_2$ (capnogram). The capnogram can be examined on a breath-by breath basis or for long term trends.

FIG. 3 shows an example capnogram waveform 300 of the exhalation phase of breathing, labelled with the relevant stages for monitoring $CO_2$. During inhalation the graph is flat, since during inhalation there is no $CO_2$ released by the patient. During exhalation, the maximum $CO_2$ is being released by the patient. The graph of the waveform may have an x-axis representing time. The y-axis may be a measurement associated with $CO_2$ concentration, such as for example, percentage of total respiratory gas (%) or partial pressure of $CO_2$ (mm Hg).

The portion of the graph between A and B represents the beginning of exhalation. Very little to no $CO_2$ is present because the gas being exhaled is from the anatomic dead space where gas exchange does not occur and hence it will have the same $CO_2$ concentration as the previously inhaled breath. The portion between B and C represents the part of exhalation where $CO_2$ from the alveoli begins to mix with the gas in the anatomic dead space, causing a rapid rise in the amount of $CO_2$ present. The portion between C and D represents the part of exhalation where $CO_2$ rich alveolar gas constitutes the majority of the exhaled air. A relatively uniform concentration of $CO_2$ from the alveoli to the nose/mouth is observed. The point D represents the end of exhalation and contains the highest concentration of $CO_2$. This is the $ETCO_2$ measurement and in a healthy individual is normally between 5-6% or 35-45 mmHg. The portion between D and E represents where inhalation begins and fresh gas fills the airway causing the $CO_2$ level to quickly drop back to near zero. This cycle then repeats, beginning again at A.

Changes in the shape of a capnogram can be diagnostic of disease conditions and changes in $ETCO_2$ can be used to assess disease severity and response to treatment. However, when canography is used in conjunction with high flow respiratory therapy, these same assessments are difficult to conduct due to the flushing mechanism of high flow therapy. A commercial high flow respiratory therapy system is commercially available from Fisher and Paykel Healthcare of Auckland NZ and marketed under the Optiflow™ trademark. An example hardware device having a humidifier with an integrated flow generator is also commercially available from Fisher and Paykel Healthcare of Auckland NZ and marketed under the AIRVO™ trademark. The high flows delivered to the patient flush the dead space in the upper airways resulting in a non-uniform distribution of $CO_2$ from the alveoli to the nose and mouth. Alveolar $CO_2$ is mixed with fresh gas from the cannula, causing a dilution of exhaled $CO_2$ that is sampled and measured. The shape of the capnogram, and in particular the phase between C and D of FIG. 3, is altered by the non-uniform distribution of $CO_2$. This can lead to an incorrect diagnosis or assumptions about disease conditions. The $ETCO_2$ naturally underestimates the $PaCO_2$, and this underestimation increases in magnitude with increasing cannula flow rate. For example, a healthy individual who receives nasal high flow respiratory therapy at 30 L/min can have reported $ETCO_2$ that is 50% lower, more preferably 80% lower than their actual value, resulting in inaccurate assessments. Compensating exhaled $CO_2$ measurements for this dilution caused by flushing would greatly enhance the usability of capnography with high flow respiratory therapy.

The present disclosure provides multiple different techniques to account for the dilution of $CO_2$ caused by high flow respiratory therapy. Each alternative technique is reliant on measuring the diluted $CO_2$ via any brand or type of capnograph. Each technique can estimate instantaneous values constantly over each breath cycle and/or estimate particular values during the breath cycle (e.g. end tidal gases $CO_2$) or over multiple breaths. Although disclosed mainly in relation to exhaled $CO_2$ measurements and specifically ET $CO_2$ measurements, the present disclosure is not limited to $CO_2$ measurements, but is applicable to other exhaled gas measurements as well. For some gases it is important to take into consideration the amount of the gas of interest that is inhaled and/or delivered to the patient when determining the exhaled gas measurement. Moreover, although disclosed mainly with respect to respiratory high flow therapy, the present disclosure is applicable to any non-sealed respiratory therapy where exhaled gas measurements are obtained. The techniques of the disclosure may be utilized with either a sealed interface or an unsealed interface. In a sealed interface, the exhaled gases may be measured with a sensor positioned in the mask or adjacent the mask. The system may have a controller, which may be able to implement a technique for distinguishing the particular interface type being utilized. The same controller, or a different controller, may be able to implement the techniques provided in this disclosure. That controller may be able to adjust the implementation of the disclosed techniques for gas measurement compensation based on the determined interface type. That controller may be able to select a technique from at least the techniques provided in this disclosure for gas measurement compensation based on the characteristics of the patient, the characteristics of the system, the characteristics of the gas being delivered, and/or the determined interface type.

Figure 4:
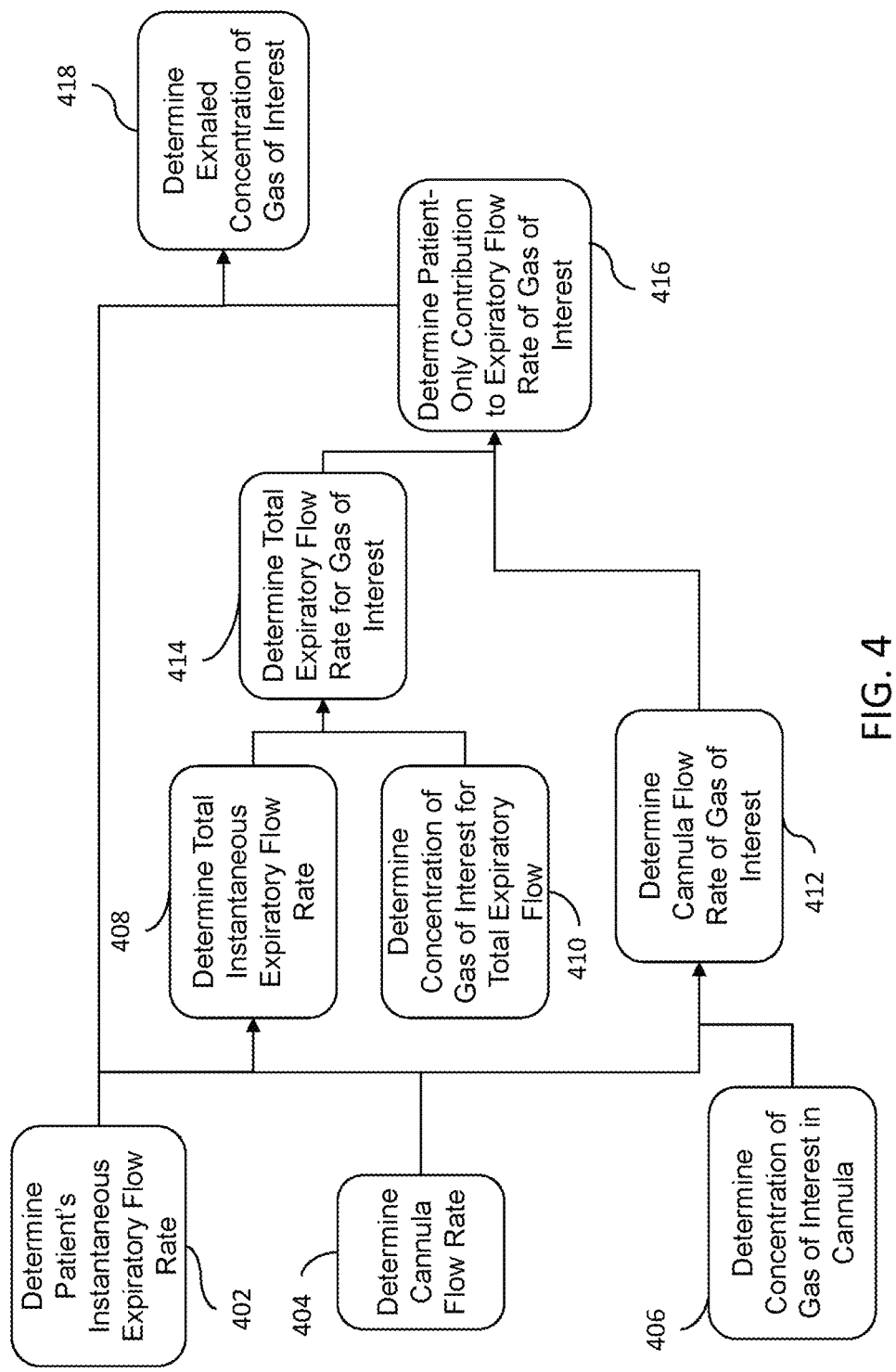
FIG. 4 is a flow chart for one technique for accounting for the dilution of respiratory gas caused by high flow respiratory therapy.

Technique 1: Flow Rate Dilution (FIG. 4)

Flow rate dilution is one way of accounting for the dilution caused by flushing with high flow respiratory therapy. The technique involves analyzing the flow rates during expiration. The total expiratory flow rate for a patient on high flow respiratory therapy at any point during expiration is the combination of the expiratory flow rate from the lungs and the cannula flow rate (also referred to as delivered flow rate) entering the nasal cavity. These flow rates can be determined, calculated and/or measured. The concentration of the respiratory gas of interest (e.g. $CO_2$, oxygen, nitrous oxide) of the total expiratory flow is the diluted value measured during high flow respiratory therapy. The concentration of the gas of interest exhaled by the patient can be determined from the measured (diluted) concentration of the gas of interest in the total expiratory flow rate, the concentration of the gas of interest in the delivered flow, the cannula flow rate and the expiratory flow rate from the lungs.

At minimum, performing flow rate dilution may require a processor and two sensors. In some embodiments, a processor and a single sensor may be utilized. The processor may perform at least some of the steps in the flow rate dilution technique. As defined above, the processor may encompass a PC, microprocessor, controller, tablet, mobile processing device, or a server. The processor may be a controller on the blower or a controller on the humidifier. A first sensor may be a capnograph, or any other sensor capable of measuring the concentration of a gas of interest in a total expiratory flow. Other suitable sensors such as $O_2$ sensor or a $N_2$ sensor or a gas chromatograph or a mass spectrometer or an end tidal gas measurement sensor can be used to measure the concentration of a gas of interest in the total expiratory flow. A second sensor may be any type of flow rate sensor capable of measuring the flow rate from the patient's lungs. In the embodiment with only two sensors, both of these sensors may be located in the same location, or locations close in proximity, such as at or within the patient interface, tubing connecting to the patient interface, and/or any connecting to the inspiratory conduit (e.g., at the Y-piece or another coupler like a swivel connector), When the cannula flow rate and concentration of the gas of interest being delivered through the cannula are both already known and remain constant, sensors needed to measure those parameters are not needed. A processor may use those known parameters in order to remove the influence of the cannula flow from the total expiratory flow, which may be calculated from measurements by the second sensor, in order to determine the portion of the total expiratory flow that is attributed only to the patient exhaling. That result may be combined with measurements from the first sensor in order to also remove the portion of the measured concentration of the gas of interest in the total expiratory flow that is attributable to the cannula flow, leaving behind only the concentration of the gas of interest expired by the patient.

Since flow rate dilution involves using the two sensors to make measurements of instantaneous flow rate and the concentration of the gas of interest at one point in time, the sampling rate of the sensors may not be a great consideration.

Instead of having a second sensor measuring the flow rate of the patient's expiration, the second sensor may instead be any pressure sensor located within the system. Instead of directly measuring a flow rate via a sensor, that flow rate may be indirectly determined using at least one pressure sensor, as discussed in U.S. Application No. 62/046,000, filed Sep. 4, 2014, titled "Methods and Apparatus for Flow Therapy", and previously incorporated herein by reference. The pressure sensor may measure a pressure parameter at some location in the flow therapy system. Based on the location of the pressure sensor, the relationship between the measured pressure parameter and the flow rate of the total expiratory flow may be known. That relationship may be determined by the processor. That relationship may be stored within a lookup table, so that the flow rate of the total expiratory flow may be quickly determined based on the measured pressure parameter.

The addition of sensors for the flow rate dilution technique may increase its accuracy and improve robustness under conditions in which parameters are changing, but are not required. For example, the cannula flow rate and the concentration of the gas of interest delivered through the cannula may be in flux. One or more additional sensors may be placed within the cannula in order to measure these parameters in real time, such as placing a flow rate sensor and a capnograph in the cannula.

FIG. 4 is a flow chart that shows how the technique of flow rate dilution can be used to calculate exhaled concentration of a respiratory gas from the patient in order to account for the dilution of respiratory gas caused by high flow respiratory therapy.

At Step 402, the patient's instantaneous expiratory flow rate is determined. A patient's instantaneous expiratory flow rate may be determined as discussed in U.S. Application No. 62/046,000, filed Sep. 4, 2014, titled "Methods and Apparatus for Flow Therapy", and previously incorporated herein by reference. Any kind of flow sensor may be used to measure a patient's expiratory flow rate, and some non-limiting examples are provided: the flow sensor may be a mechanical flow meter, such as a turbine flow meter, air flow meters, anemometers, and so forth; the flow sensor may be a pressure-based meter, such as a differential pressure manometer, pitot tubes, and so forth; the flow sensor may be an optical flow meter, which may use laser-based interferometry to measure the speed of the respiratory gas particles; the flow sensor may be an ultrasonic flow meter, which may use the photoacoustic Doppler effect and measure the velocity of a fluid using ultrasound.

At Step 404, the cannula flow rate, or the rate of air flow being delivered to the patient via the cannula, is determined. This may be done using the sensors or techniques described in Step 402 for measuring the patient's instantaneous expiratory flow rate, since the desired measurement of Step 404 is also the instantaneous flow rate of air within a tube. The instantaneous cannula flow rate may be measured. However, in some cases the cannula flow rate may be a constant, or it may be pre-set at a known level. During the high flow therapy, a specific cannula flow rate may be chosen for delivering air to the patient. This chosen cannula flow rate may be known beforehand, so estimating the cannula flow rate at Step 404 may simply involve taking the known cannula flow rate.

At Step 408, the total instantaneous expiratory flow rate may be calculated from the patient's instantaneous expiratory flow rate and the instantaneous cannula flow rate. There may be a generalized equation that relates the total instantaneous expiratory flow to the measured instantaneous patient expiratory flow and cannula flow rate. If Qp represents the instantaneous patient expiratory flow and Qc represents cannula flow rate, such a generalized equation may be represented by the function Qe=f(Qp, Qc), where Qe is the total instantaneous expiratory flow rate. In some embodiments, the equation may be an addition function such that total instantaneous expiratory flow rate is calculated by adding the instantaneous patient expiratory flow with the cannula flow rate. The equation may be represented as Qe=Qp+Qc.

At Step 410, the concentration of the gas of interest for the total expiratory flow may be measured. In equations, this measured concentration of the gas of interest for the total expiratory flow can be represented as Ce. This measurement may be performed by a capnograph, such as the one shown in FIG. 2. The capnograph may monitor the concentration or partial pressure of the gas of interest, which may be a component of a mixture of gases. For example, the gas of interest may be any singular respiratory gas that is a component of air. The gas of interest may be $CO_2$. However in this situation, this measured concentration of $CO_2$ for total expiratory flow may underestimate the $PaCO_2$ during high flow therapy as described above in the discussion for FIG. 3. Further steps are needed in order to adjust this measurement in order to reduce the influence of the additional $CO_2$ delivered by the cannula, leaving only the portion of the $CO_2$ concentration attributable to the patient's expiration.

At Step 414, the total expiratory flow rate for the gas of interest may be calculated. The total instantaneous expiratory flow rate, determined at Step 408, may be multiplied with the measured concentration of the gas of interest for the total expiratory flow, determined at Step 410, in order to calculate the total expiratory flow rate for the gas of interest. In equation form, the total expiratory flow rate of the gas of interest may be represented as $Qe_{,gas}$. Thus, the total expiratory flow rate for $CO_2$ could be represented as $Qe_{,CO2}=Qe \times Ce$. This total expiratory flow rate for the gas of interest, $Qe_{,gas}$, is also a sum of two components: the cannula flow rate of the gas of interest and the patient-only expiratory flow rate of the gas of interest. If the cannula flow rate of the gas of interest can be determined, that value can be subtracted from the total cannula flow rate of the gas of interest in order to obtain the patient-only expiratory flow rate of the gas of interest, which is helpful in calculating the actual exhaled concentration of the gas of interest from the patient, or $ETCO_2$ as described above.

At Step 406, the concentration of the gas of interest in the cannula flow is measured. The first capnography may be able to measure the inspiratory gas concentration which would be the concentration of the gas of interest in the cannula. Another technique of measuring this is to have a separate, second capnograph that monitors only the gas in the cannula. The second capnograph can be used to directly measure the concentration of the gas of interest in the cannula. Alternatively, a different type of sensor could be used that specifically measures the concentration of the gas of interest, either directly or indirectly. In some embodiments, the concentration of the gas of interest in the cannula is pre-set or known, and the known concentration of the gas of interest within the cannula can be used rather than having to measure the concentration. For example, the cannula may be configured to deliver pure oxygen. If the gas of interest is $CO_2$, then the concentration of $CO_2$ in the cannula would be zero. As another example, the cannula may be configured to deliver air. The composition of air is approximately 78% nitrogen, 21% oxygen, and 0.03% $CO_2$. The composition of air may be used to indirectly determine the concentration of $CO_2$ in the cannula. In equation form, the concentration of the gas of interest in the cannula may be represented as Cc.

At Step 412, the cannula flow rate of the gas of interest may be calculated. The cannula flow rate of the gas of interest may be calculated by multiplying the concentration of the gas of interest in the cannula flow, determined at Step 406, by the cannula flow rate, determined at Step 404. In equation form, the cannula flow rate of the gas of interest may be represented as $Qc,_{gas}$. If the gas of interest is $CO_2$, then $Qc,_{Co2}$=Qc×Cc.

At Step 416, the patient-only contribution to expiratory flow rate of the gas of interest can be calculated, as previously mentioned, by subtracting the cannula flow rate of the gas of interest from the total expiratory flow rate for the gas of interest. In equation form, patient-only contribution to expiratory flow rate of the gas of interest may be represented as $Qp,_{gas}$. If the gas of interest is $CO_2$, then $Qp,_{Co2}$=$Qe,_{Co2}$−$Qc,_{Co2}$.

At Step 418, the exhaled concentration of the gas of interest, which can be represented as Cp, can be calculated as a percentage by dividing the patient-only contribution to expiratory flow rate of the gas of interest (calculated at Step 416) by the patient's expiratory flow rate (measured at Step 402), and then multiplying that result by 100.

An example calculation for $CO_2$ as the gas of interest using the flow rate dilution technique of FIG. 4 is provided below:

1) Determined instantaneous patient expiratory flow, Qp=20 L/min
2) Cannula flow rate, Qc=40 L/min
3) Determined total instantaneous expiratory flow, Qe=Qp+Qc=60 L/min
4) Measured gas of interest ($CO_2$) concentration, Ce=2%
5) Total expiratory $CO_2$ flow rate, $Qe,_{CO2}$=Qe×Ce=1.2 L/min
6) Concentration of the CO2 in the cannula flow, Cc=0.03%
7) Flow rate of CO2 from the cannula, $Qc,_{CO2}$=Qc×Cc=0.012 L/min
8) Patient only contribution to expiratory CO2 flow rate, $Qp,_{CO2}$=$Qe,_{CO2}$−$Qc,_{CO2}$=1.188 L/min
9) Exhaled $CO_2$ concentration, Cp=$Qp,_{CO2}$/Qp*100=5.94%

Figure 5:
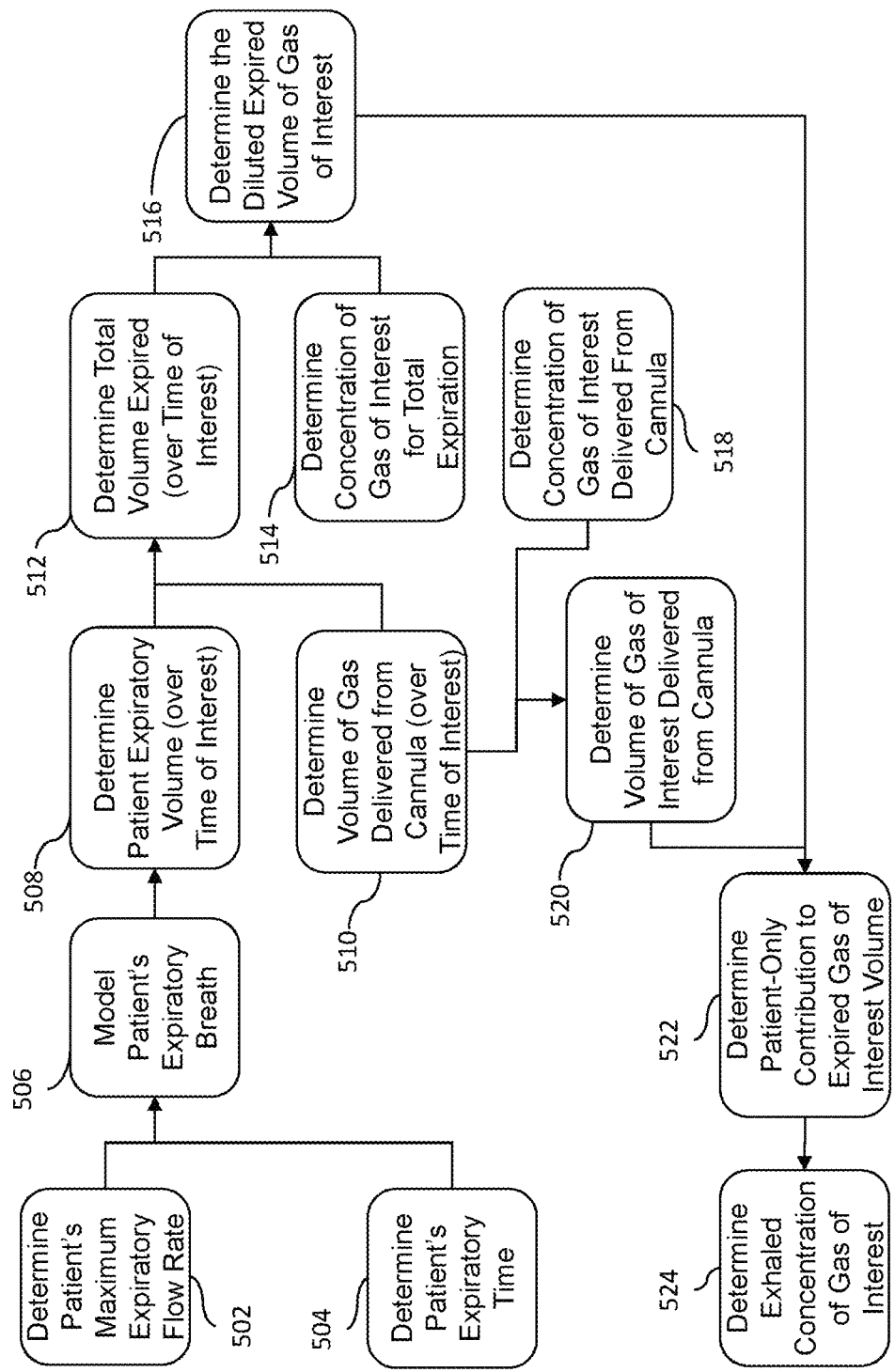
FIG. 5 is a flow chart for one technique for accounting for the dilution of respiratory gas caused by high flow respiratory therapy.
Figure 6:
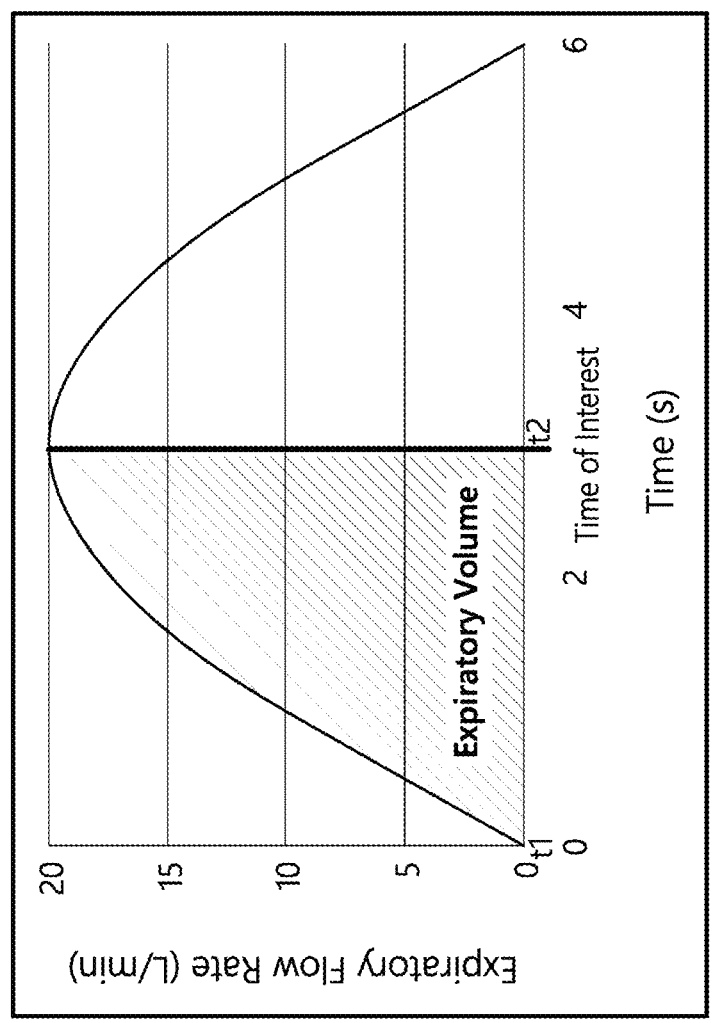
FIG. 6 illustrates an expiratory breath waveform to show how expiration can be modelled as a sine wave to estimate expiratory volume.

Technique 2: Volume Dilution (FIGS. 5 and 6)

Volume dilution is another way of accounting for the dilution caused by flushing with high flow respiratory therapy. The technique involves utilizing a key relationship: the total expired volume of gas for a high flow respiratory therapy patient at any point during expiration is the combined sum of the expiratory volume from the patient's lungs and the volume of gas delivered from the cannula. These volumes can be measured or calculated and then used to calculate the patient-exhaled concentration of the gas of interest.

The concentration of the gas of interest in the total expired volume is the diluted value measured. The concentration of the gas of interest exhaled by the patient can be determined from the measured (diluted) concentration of the gas of interest in the total expired volume, the concentration of the gas of interest in the volume of gas delivered from the cannula, the volume of gas delivered from the cannula and the patient expired volume from the lungs.

At minimum, performing volume dilution may require a processor and two sensors. The processor may perform at least some of the steps in the Volume Dilution technique. A first sensor may be a capnograph, or any other sensor capable of measuring the concentration of a gas of interest in a total expiratory flow. A second sensor may be any type of flow rate sensor capable of measuring the flow rate from the patient's lungs.

The second sensor is used to determine the patient's maximum flow rate in a single expiratory cycle. If this second sensor is a flow rate sensor, it may have to be capable of sampling flow rates over a period of time with a high enough sampling rate to determine the maximum flow rate over that period with reasonable accuracy. A processor may be used to perform signal processing on the measurements from the second sensor in order to determine the patient's breathing cycle and what measurements constitute a single expiratory cycle. This can be used to determine a patient's expiratory time. Alternatively, user input may be used in order to start and stop measurements at the beginning and end of the patient's respiratory cycle. The user would be manually estimate the patient's expiratory time, and the maximum flow rate would be taken over that time period. Alternatively, a third sensor may be used to monitor the breathing cycle and determine the patient's expiratory cycle. For example, the third sensor may be a pressure sensor that allows measuring when a patient switches from inhaling to exhaling, and vice versa. That information can be used to determine the patient's expiratory time for a single expiratory breath and used to determine the maximum expiratory flow rate over that period. However, this process may be done with the second sensor rather than an additional third sensor by monitoring variability in flow.

In the embodiment with only two sensors, both of these sensors may be located in the same location, or locations close in proximity, such as at or within the patient interface, tubing connecting to the patient interface, and/or any connecting to the inspiratory conduit (e.g., at the Y-piece or another coupler like a swivel connector), When the cannula flow rate and concentration of the gas of interest being delivered through the cannula are both already known and remain constant, sensors needed to measure those parameters are not needed. A processor may use those parameters in order to calculate the volume of gas delivered by the cannula. The processor may also use the determined maximum flow rate from the second sensor and the patient's expiratory time in order to determine the patient expiratory volume over a time of interest. That result can be combined with the concentration of a gas of interest for the total expiratory flow measured by the first sensor in order to determine the total volume of the gas of interest. The portion of the total volume of the gas of interest attributable to the cannula flow may be removed or reduced, leaving behind only the patient contribution to the total volume of the gas of interest, which may then be converted into a concentration.

However, if cannula flow rates and/or concentrations of the gas of interest delivered from the cannula are in flux over this sampling period, then additional sensors would be needed to measure these two parameters over the sampling period. A processor may have to determine the area under the measure curve of the cannula flow rates to determine the total volume of gas delivered by the cannula. To determine the portion of the concentration of gas of interest in the total expiratory flow attributable to the cannula flow, a processor may also have to factor in both the changing concentrations of the gas of interest delivered by the cannula as well, such as by determining an average delivered concentration of the gas of interest by the cannula. For improved accuracy, the processor may need to factor in the changing cannula flow rate into that calculation. Thus, these additional sensors for the volume dilution technique may improve its accuracy and improve robustness under conditions in which parameters are changing Compared to flow rate dilution, volume dilution requires monitoring and sampling patient expiratory flow rates over a large enough period of time to encapsulate the patient's entire expiratory cycle, which allows for determining the maximum expiratory flow rate.

FIG. 5 is a flow chart that shows how the technique of volume dilution can be used to calculate exhaled concentration of a respiratory gas in order to account for the dilution of respiratory gas caused by high flow respiratory therapy.

At Step 502, the patient's maximum expiratory flow rate is measured. The patient's maximum expiratory flow rate is the maximum flow rate observed in a single expiratory breath. This patient's maximum expiratory flow rate can be measured as described above with respect to the technique of flow rate dilution of FIG. 4, and may involve the use of a flow meter. The patient's maximum expiratory flow rate may be represented as Qpe in equation form.

At Step 504, the patient's breath pattern can be monitored to determine the patient's expiratory time. The patient's expiratory time may be the duration of the single expiratory breath that was observed and used to determine the patient's maximum expiratory flow rate in Step 502. This expiratory time may be represented as Tp in equation form.

At Step 506, the patient's maximum expiratory flow rate and the patient's expiratory time may be used as parameters to model the patient's expiratory breath. The patient's expiratory breath may be modelled on any function or set of assumptions. The patient's expiratory breath may be assumed to follow half of a sine wave, such as in the graph shown in FIG. 6. The patient's maximum respiratory flow rate is the amplitude and the patient's expiratory time is the half period. A sine equation can be modeled that meets those constraints. In some embodiments, the patient's expiratory breath may be modelled by a combination of equations, such as a piecewise model. In some embodiments, the patient's expiratory breath may be modelled by a combination of sine equations and/or periodic functions. A more accurate waveform will yield more accurate results. For example, the expired volume can be calculated using trapezoid approximations, instead of a sine wave. Over short periods of time, patient expiratory flows at 2 points in time can be used. Multiple volumes can be calculated over the breath (and matched up with the corresponding varying Ce) in order to determine how the $CO_2$ varies over time. This is described in further detail below with respect to Technique 3 and FIG. 7. In an alternative embodiment, sampling may be performed at one or more points during expiration that are not the point of maximum expiratory flow. These values may be used to create a sine wave model that is curve fit to those points. For example, if the expiratory time period was 6 seconds and an expiratory flow of 10 L/min at 1 second from the start of expiration was measured, then at least that data point may be used in creating a sine wave model that fits at least that data point.

At Step 508, the patient expiratory volume over the time of interest is determined. To do this, the modelled function from Step 506 can be integrated between two points of interest in time to calculate the area under the curve, which corresponds to an estimation of the volume that has been expired between the two points of interest in time. An example of this is shown in FIG. 6. For the time period of interest, the first point of time may be represented as t1 and the second point of time may be represented as t2. Integrating the function to estimate patient expiratory volume over the time of interest would utilize the following equations:

$$V_p = \int_{t_1}^{t_2} Q_{pe} \cdot \sin\left(\frac{\pi t}{T_p}\right) dt$$

$$V_p = \left[-Q_{pe} \cdot \frac{T_p}{\pi} \cos\left(\frac{\pi t}{T_p}\right)\right]_{t_1}^{t_2}$$

$$V_p = Q_{pe} \cdot \frac{T_p}{\pi} \cos\left(\frac{\pi t_1}{T_p}\right) - Q_{pe} \cdot \frac{T_p}{\pi} \cos\left(\frac{\pi t_2}{T_p}\right)$$

At Step 510, the volume of gas delivered by the cannula during the time of interest is calculated. One way of doing this is to measure the volume of gas that is delivered through the cannula over the time of interest, although that may be quite difficult to do. Another way is to measure the instantaneous cannula flow rate over the time of interest, and use that information to indirectly determine the volume of gas delivered. For example, a processor could make many samples of the instantaneous cannula flow rate over the time of interest to produce a graph, and then the processor could determine the area under the graph in order to determine the volume (such as through trapezoidal approximation). Another way is similar to Step 506 and model the flow rates through the cannula over the time of interest, and then determine the area under the graph of the model. However, in many cases the flow rate of the cannula is well-known or set in advance. For high flow therapy, a specific cannula flow rate may be chosen to treat each patient. That flow rate may be a constant that can be multiplied with the duration of the time of interest in order to determine the volume of gas delivered over that duration. The delivered cannula flow rate may be represented as Qc, which may be a constant. The volume of gas delivered by the cannula may be represented as Vc in an equation, with Vc=Qc.t2−Qc.t1.

At Step 512, the patient expiratory volume over the time of interest is added to the volume of gas delivered by the cannula over the time of interest in order to calculate the total volume expired over the time of interest. The total volume expired may be represented as Ve, such that Ve=Vp+Vc. Plugging in the appropriate formulas for Vp and Vc shows that Ve can be calculated as follows:

$$V_e = Q_{pe} \cdot \frac{T_p}{\pi} \cos\left(\frac{\pi t_1}{T_p}\right) - Q_{pe} \cdot \frac{T_p}{\pi} \cos\left(\frac{\pi t_2}{T_p}\right) + Q_c t_2 - Q_c t_1$$

At Step 514, the concentration of the gas of interest for the total expiration may be measured. This may be performed as described in Step 410 of FIG. 4. This may be performed through the use of a capnograph to measure the concentration of the gas of interest. For example, the capnograph may directly measure the concentration or partial pressure of $CO_2$ for the total expiration. The measured concentration of the gas of interest across the time period of interest may be represented as Ce.

At Step 516, the diluted expired volume of the gas of interest may be calculated by multiplying the total volume expired over the time of interest by the measured concentration of the gas of interest for the total expiration, obtained from Step 514. The diluted expired volume of the gas of interest may be represented by $Ve,_{gas}$, such that $Ve,_{CO2}$=Ve×Ce.

At Step 518, the concentration of the gas of interest delivered through the cannula may be measured. This may be done through the techniques described in Step 406 in FIG. 4. In many cases, the concentration of the gas of interest delivered through the cannula will be constant over the time period. However, if it is not constant, then the average concentration for that time period may need to be determined, or a different time of interest may need to be selected altogether for which the concentration does remain a constant. In many cases, the concentration of the gas of interest delivered through the cannula will be known or can be assumed. For example, if the gas of interest is $CO_2$ and the cannula is used to deliver air, then the concentration of $CO_2$ over the time of interest will be approximately 0.03%. The concentration of the gas of interest delivered through the cannula may be represented as Cc.

At Step 520, the volume of the gas of interest delivered through the cannula can be calculated by multiplying the total volume of gas delivered through the cannula (calculated at Step 510) and the concentration of the gas of interest delivered through the cannula (calculated at Step 518). The volume of the gas of interest delivered through the cannula may be represented by $VC,_{gas}$ so that if $CO_2$ is the gas of interest, the equation would be $VC,_{CO2}$=Vc×Cc.

At Step 522, the patient-only contribution to the expired gas of interest volume can be calculated by subtracting the volume of the gas of interest delivered from the cannula (calculated at Step 520) from the diluted expired volume of the gas of interest (calculated at Step 516). This patient-only contribution to expired gas of interest volume may be represented as Vp,gas. For example, $Vp,_{CO2}$=$Ve,_{CO2}$−$VC,_{CO2}$.

At Step 524, the exhaled concentration of the gas of interest can be calculated by dividing the patient-only contribution of the expired gas of interest volume (calculated at Step 522) by the patient's expiratory volume (calculated at Step 508) and multiplying that result by 100. For example, the exhaled $CO_2$ concentration may be represented as Cp, which is calculated by Cp=$Vp,_{CO2}$/VP*100.

An example calculation for $CO_2$ as the gas of interest using the volume dilution technique of FIG. 5 is provided below:

1) Determined maximum patient expiratory flow rate, Qpe=20 L/min
2) Delivered cannula flow rate, Qc=30 L/min
3) Expiratory time, Tp=6 seconds=6/60 minutes
4) Measured $CO_2$ concentration across time period of interest, Ce=1.5%
5) Patient Expiratory volume, $$V_p = \int_{t_1}^{t_2} Q_{pe} \cdot \sin\left(\frac{\pi t}{T_p}\right) dt$$

$$V_p = \left[-Q_{pe} \cdot \frac{T_p}{\pi} \cos\left(\frac{\pi t}{T_p}\right)\right]_{t_1}^{t_2}$$

$$V_p = Q_{pe} \cdot \frac{T_p}{\pi} \cos\left(\frac{\pi t_1}{T_p}\right) - Q_{pe} \cdot \frac{T_p}{\pi} \cos\left(\frac{\pi t_2}{T_p}\right)$$

6) Time period of interest, t1=0 seconds=0 minutes, t2=3 seconds=3/60 minutes
7) Delivered cannula volume, Vc=Qc.t2−Qc.t1
8) Total volume expired, Ve=Vp+Vc $$V_e = Q_{pe} \cdot \frac{T_p}{\pi} \cos\left(\frac{\pi t_1}{T_p}\right) - Q_{pe} \cdot \frac{T_p}{\pi} \cos\left(\frac{\pi t_2}{T_p}\right) + Q_c t_2 - Q_c t_1$$

Ve=2.14 L
9) Diluted expired volume of $CO_2$, $Veco_2$=Ve×Ce=0.032 L
10) Concentration of $CO_2$ delivered from cannula, Cc=0.03%
11) Delivered volume of $CO_2$ from the cannula, $VCCO_2$=Vc×Cc=0.00045 L
12) Patient only contribution to expired $CO_2$ volume, $VpCO_2$=$VeCO_2$−$VCCO_2$=0.03155 L
13) Exhaled $CO_2$ concentration, Cp=$VpCO_2$/Vp*100=4.96%

FIG. 6 illustrates an expiratory breath waveform to show how expiration can be modelled as a sine wave to estimate expiratory volume. The waveform corresponds to the sample calculation shown above. The peak expiratory flow rate is 20 L/min. The expiratory time is 6 seconds, but the time of interest is only the first three seconds. The expiratory volume for those first three seconds is calculated by measuring the area under the curve.

Figure 7:
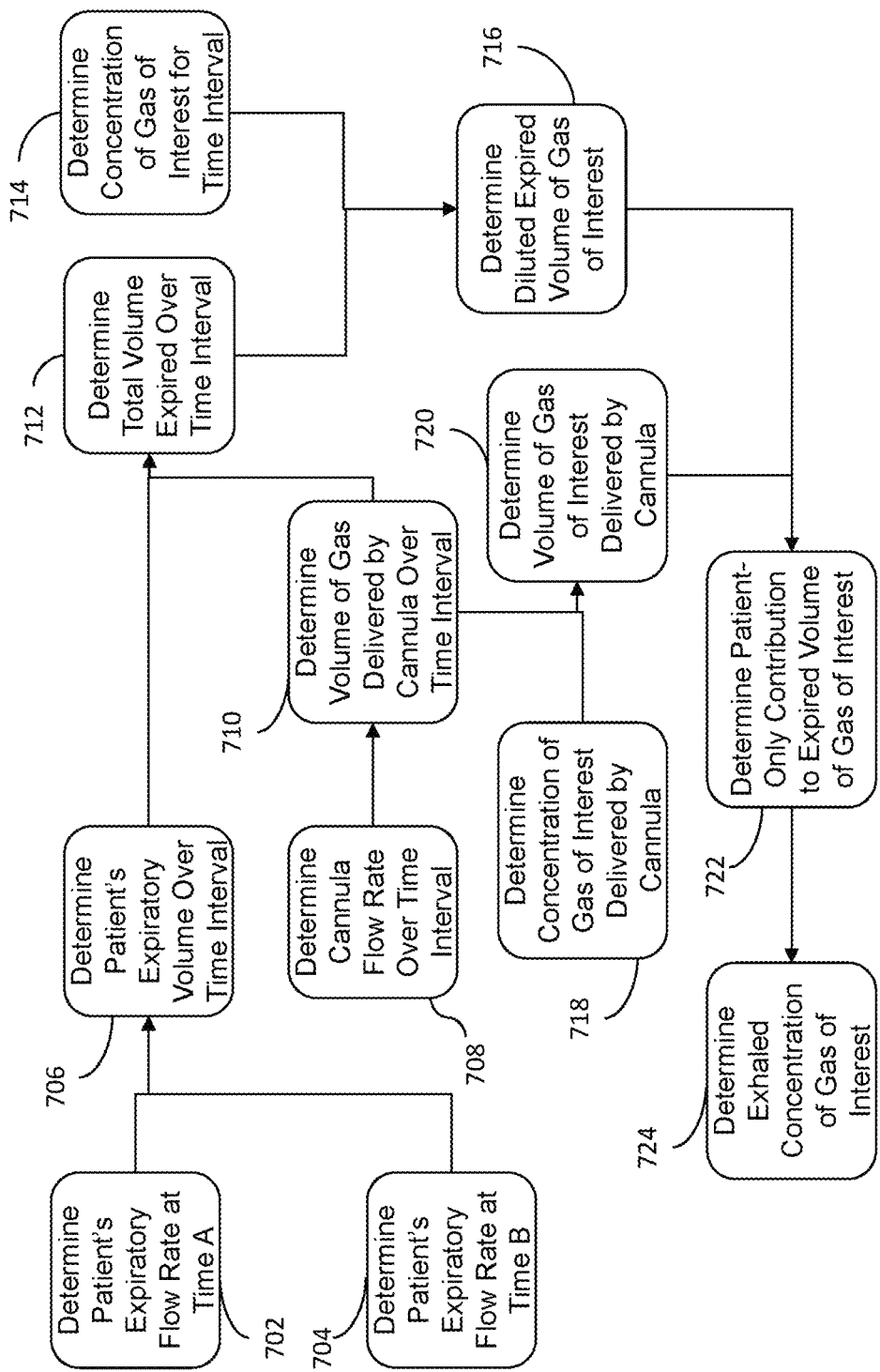
FIG. 7 is a flow chart for one possible technique for accounting for the dilution of respiratory gas caused by high flow respiratory therapy.
Figure 8:
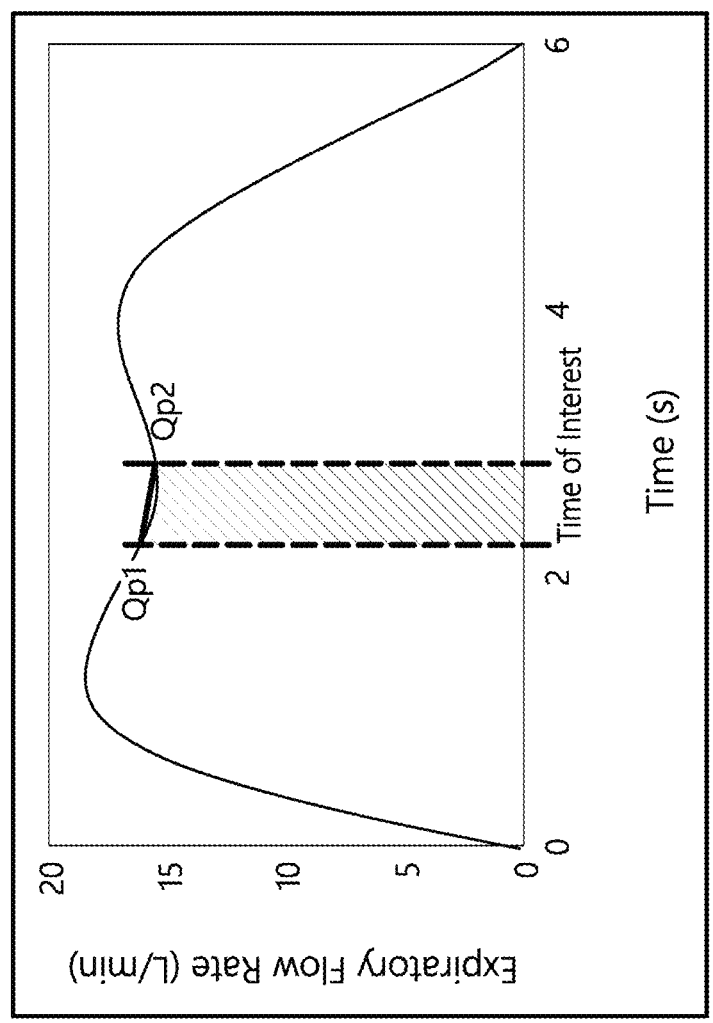
FIG. 8 illustrates how expiratory volume over a time interval can be determined by trapezoidal approximation.

Technique 3: Volume Dilution & Integral Approximation (FIGS. 7 and 8)

A variation on the volume dilution technique described in Technique 2 allows for the accounting for the dilution caused by flushing with high flow respiratory therapy. The volume dilution technique with integral approximation allows for the accurate calculation of expiratory volume, which is used to calculate the patient-exhaled concentration of the gas of interest.

Performing volume dilution with integral approximation has the same minimum hardware requirements as disclosed in the description of Technique 2 above. However, the use of integral approximation as opposed to generating a mathematical model for integration means that the sampling rate of the second sensor must be high enough to catch granular changes in patient expiratory flow rate over the desired time interval, which is typically a very short period of time. The processor may also perform more instructions by performing the integral approximation and/or choosing the time interval over which to perform the integral approximation.

If cannula flow rates and/or concentrations of the gas of interest delivered from the cannula are in flux over the sampling period, then additional sensors would be needed to measure these two parameters over the sampling period. However, these additional sensors would also need to sample in-sync with the second sensor since this technique utilizes the volume of gas the gas of interest delivered by the cannula over the same time interval that the integral approximation of patient expiratory volume was performed on.

FIG. 7 is a flow chart that shows how the technique of volume dilution with integral approximation can be used to calculate exhaled concentration of a respiratory gas in order to account for the dilution of respiratory gas caused by high flow respiratory therapy.

As mentioned above in the description of Technique 2, the expired volume can be calculated using integral approximation rather than modeling the expiratory breath with a sine wave. The instantaneous flow rate over a duration of time can be sampled and interpolated into a curve. For short periods of time, the area under the curve can be approximated in order to estimate the expired volume over that short period of time.

One way of performing the integral approximation is using trapezoid approximations, which only requires the patient expiratory flows at two points in time within a short duration of time. However, this is only one manner of doing integral approximation. Trapezoidal approximation has the advantage of being accurate for the integration of periodic functions over their periods and only requiring the flow rate values at two points. However, in some embodiments a different technique of numerical integration and approximation may be used instead. A different Newton-Cotes formula may be used, some examples including Simpson's rule, Simpson's 3/8 rule, and Boole's rule. Other techniques, such as Gaussian quadrature and Clenshaw-Curtis quadrature may be used for improved accuracy on non-periodic functions. The use of other integral approximation techniques may allow for a reasonably accurate approximation for longer time durations.

Referring back to FIG. 7, at Step 702 the patient's maximum expiratory flow rate is measured at a Time A. At step 704, the patient's maximum expiratory flow rate is measured at a Time B. The combined result is measuring the patient's maximum expiratory flow rate at two different points in time over a short period. This measurement may be performed using the techniques and devices discussed above with respect to Technique 1. The first flow rate may be represented as Qp1 and the second flow rate may be represented as Qp2. Time A may be represented as t1 and Time B may be represented as t2.

At Step 706, the patient expiratory volume over this short time interval is approximated by integrating the area of a trapezoid constrained by the two flow rates and the time interval. An example of this is shown in FIG. 8. The patient expiratory volume may be represented as Vp, so that its calculation is as follows:

$$V_p = \left[\left(\frac{Qp1 + Qp2}{2}\right) \cdot (t2 - t1)\right]$$

From there, the rest of the technique is similar to Technique 2. At Step 708, the cannula flow rate is measured over the time interval. The cannula flow rate may be represented as Qc. The cannula flow rate may be pre-set or already known, and thus it may not need to be measured.

At Step 710, the cannula flow rate is used to calculate the volume of gas delivered by the cannula over the time interval. This can be done using modelling or integral approximation as disclosed herein, but most commonly the cannula flow rate will be a constant. The total volume of gas delivered by the cannula (Vc) can just be obtained by multiplying the cannula flow rate with the time interval, such that Vc=Qc.t2−Qc.t1.

At Step 712, the total volume expired over the time interval is calculated by adding the volume of gas delivered by the cannula with the patient's expiratory volume. The total volume expired may be represented as Ve, such that Ve=Vp+Vc. Ve may also be calculated as:

$$V_e = \left[\left(\frac{Qp1 + Qp2}{2}\right) \cdot (t2 - t1) + Q_c t_2 - Q_c t_1\right]$$

At Step 714, the concentration of the gas of interest may be measured for the time interval. This may be done using a capnograph. The concentration of the gas of interest may be represented as Ce.

At Step 716, the diluted expired volume of the gas of interest is calculated by multiplying the total volume expired over the time interval by the concentration of the gas of interest for the time interval. The diluted expired volume of the gas of interest may be represented as $Ve_{,gas}$, so that $Ve_{,CO2}=Vc \times Cc$.

At Step 718, the concentration of the gas of interest delivered by the cannula may be measured. In many cases this will be constant or already known. This concentration of the gas of interest delivered by the cannula may be represented as Cc.

At Step 720, the volume of the gas of interest delivered by the cannula may be calculated by multiplying the concentration of the gas of interest delivered by the cannula by the volume of total gas delivered by the cannula over the time interval. The volume of the gas of interest delivered by the cannula may be represented as $VC_{,gas}$, such that $VC_{,CO2}=Vc \times Cc$.

At Step 722, the patient-only contribution to expired volume of gas of interest may be calculated by subtracting the volume of gas of interest delivered by cannula (calculated at Step 720) from the diluted expired volume of gas of interest (calculated at Step 716). The patient-only contribution to expired volume of gas of interest may be represented by $Vp_{,gas}$, or $Vp_{,CO2}=Ve_{,CO2}-VC_{,CO2}$.

At Step 724, the exhaled concentration of the gas of interest may be calculated by dividing the patient-only contribution of the expired gas of interest volume by the patient's expiratory volume and multiplying that result by 100. For example, the exhaled $CO_2$ concentration may be represented as Cp, which is calculated by Cp=Vp,CO2/VP*100.

An example calculation for $CO_2$ as the gas of interest using the volume dilution and integral approximation technique of FIG. 7 is provided below:

1) Determined maximum patient expiratory flow rate at two points in time, Qp1=20 L/min, Qp2=17 L/min
2) Delivered cannula flow rate, Qc=30 L/min 3) Measured $CO_2$ concentration across time period of interest, Ce=1.5%
4) Patient Expiratory volume, $$V_p = \left[\left(\frac{Qp1 + Qp2}{2}\right).(t2 - t1)\right]$$

5) Time period of interest, t1=2.5/60 minutes, t2=3/60 minutes
6) Delivered cannula volume, Vc=Qc.t2−Qc.t1
7) Total volume expired, Ve=Vp+Vc $$V_e = \left[\left(\frac{Qp1 + Qp2}{2}\right).(t2 - t1) + Q_c t_2 - Q_c t_1\right]$$

Ve=0.4 L
8) Diluted expired volume of $CO_2$, $Ve_{,CO2}$=Ve× Ce=0.0061 L
9) Concentration of $CO_2$ delivered from cannula, Cc=0.03%
10) Delivered volume of $CO_2$ from the cannula, $VC_{,CO2}$=Vc×Cc=0.00075 L
11) Patient only contribution to expired $CO_2$ volume, $Vp_{,CO2}$=$Ve_{,CO2}$−$VC_{,CO2}$=0.006 L
12) Exhaled $CO_2$ concentration, Cp=$Vp_{,CO2}$/Vp*100=3.88%

The measured gas of interest concentration across the time period of interest, Ce, in the examples above can be an average across that time period. As the expired gas concentration may vary over the breath it is also possible to calculate multiple gas volumes across one breath (instantaneous volumes), and estimate the varying exhaled gas concentration. These smaller intervals can also be used to find the average or peak exhaled gas concentration over the breath, or a portion of the breath cycle. In some embodiments, as an alternative to a determined gas measurement, the analysis can be changed to obtain an average or mean gas concentration over the expired breath or an average gas concentration over the analysis period. In addition, or alternatively, an instantaneous gas concentration measurement can be obtained by using small time periods for the integral.

FIG. 8 illustrates how expiratory volume over a time interval can be determined by trapezoidal approximation. The trapezoid that is being approximated is constrained by Qp1, Qp2, t1, and t2.

Figure 9:
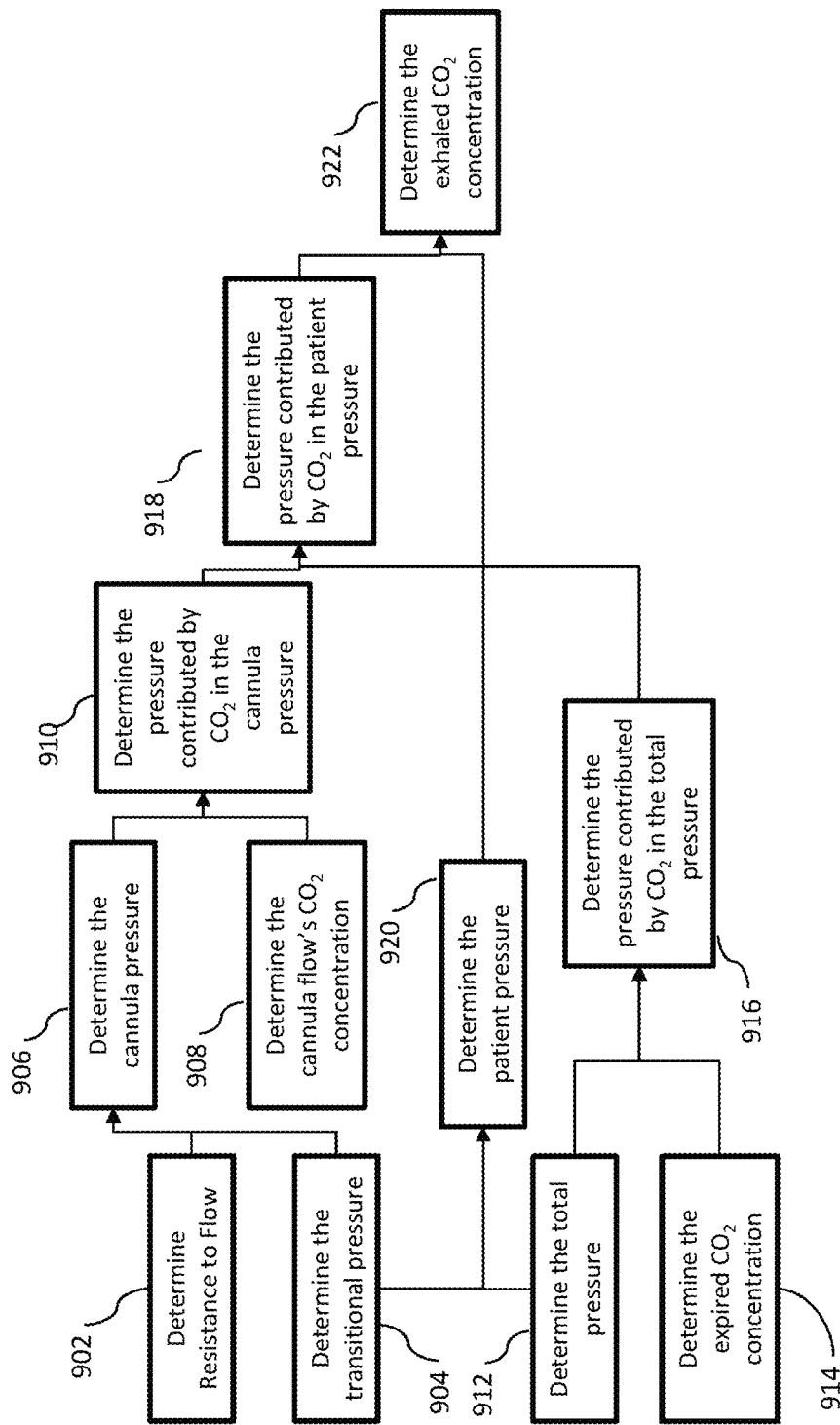
FIG. 9 is a flow chart for one possible technique for accounting for the dilution of respiratory gas caused by high flow respiratory therapy.

Technique 4: Pressure Dilution (FIGS. 9 and 10)

Pressure dilution is another way of accounting for the dilution caused by flushing with high flow respiratory therapy. The technique involves monitoring the pressures involved during expiration. The total expiratory pressure for a patient on high flow respiratory therapy at any point during expiration is the combination of the expiratory pressure from the patient, the pressure from the cannula flow, and the pressure caused by the resistance to flow of the hardware in the flow therapy system. The pressure from the cannula flow is the pressure that is generated due to the flow from the nasal cannula when the cannula are engaged with the nares. This pressure is determined when the cannula is engaged with the patient and can be measured using a pressure sensor. It may be measured anywhere in the system, either at the patient interface (for example, at the cannula) or anywhere else along the system. The hardware may include the conduit, cannula, patient interface, flow generator, and so forth. The transitional pressure for a patient on high flow respiratory therapy is the pressure at which there is no contribution from the patient breathing. It is therefore a combination of the pressure from the cannula flow, and the pressure caused by the resistance to flow of the hardware. These pressures can be determined and measured. The concentration of the respiratory gas of interest (e.g., $CO_2$, oxygen, nitrous oxide, nitrogen) of the total expiratory pressure is the diluted value measured during high flow respiratory therapy. The concentration of the gas of interest exhaled by the patient can be determined from the measured (diluted) concentration of the gas of interest in the total expiratory pressure and its components.

At minimum, performing pressure dilution may require a processor and two sensors. The processor may perform at least some of the steps in the Pressure Dilution technique. A first sensor may be a capnograph, or any other sensor capable of measuring the concentration of a gas of interest in a total expiratory flow. The second sensor may be any type of pressure sensor capable of determining the total expiratory pressure.

The second sensor is used to determine the total expiratory pressure over a breathing cycle. The second sensor has to have a high enough sampling rate to determine the inflection point or transitional pressure, at which the total expiratory pressure is just a combination of pressure from the cannula flow and the pressure caused by the resistance to flow of the hardware. A processor may use signal processing in order to determine the transitional pressure. The second sensor may need to be placed at specific locations within the flow therapy system in order to measure the total expiratory pressure. The second sensor could be placed in the cannula, tubing or by the humidification chamber. The second sensor may be anywhere in the flow therapy system. [0113]The pressure caused by the resistance to flow of the hardware may be known beforehand or determined based on a specific hardware combination, which may also allow the pressure from the cannula flow to be known. The cannula flow pressure may be constant, along with the concentration of the gas of interest being delivered by the cannula. However, if these parameters are not known then more sensors may be needed. If the cannula flow rate is in flux then the cannula flow pressure may be changing as well. Additional pressure sensors may be used to measure in real-time the pressure from the cannula flow and/or the pressure caused by the resistance to flow of the hardware. An additional capnograph or gas concentration sensor may be used to measure in real-time the concentration of the gas of interest being delivered by the cannula. Alternatively, pressure measurements may be taken using just the second sensor to take a first measurement with the patient wearing the nasal cannula and patient interface, and then taking a second measurement with the patient not wearing the nasal cannula and patient interface.

FIG. 9 is a flow chart that shows how the technique of pressure dilution can be used to calculate exhaled concentration of a respiratory gas in order to account for the dilution of respiratory gas caused by high flow respiratory therapy.

At Step 902, the pressure due to resistance of flow (hardware pressure) is measured. Techniques to do this are covered in U.S. Application No. 62/046,000, filed on Sep. 4, 2014, titled "Methods and Apparatus for Flow Therapy", and previously incorporated herein by reference. The pressure caused by the resistance to flow of the hardware may be represented by PH.

At Step 904, the transitional pressure for the patient is measured or determined from a point in the hardware downstream of the flow source. The transitional pressure for a patient on high flow respiratory therapy is the pressure at which there is no contribution from the patient breathing. It represents the sum of pressures of the pressure from the cannula flow, and the pressure caused by the resistance to flow of the hardware. The transitional pressure may be represented by PT.

This can be done by measuring the pressure at the point of transition between inspiration and expiration, or vice versa. An example of how the transitional pressure can be identified in this manner is shown in FIG. 10. This technique would involve breath detection. Alternatively, the total expiratory pressure at point A can be measured across multiple breaths, and the mean can be calculated. This has been shown to be equivalent to the transitional pressure measured by the first technique. As another alternative, the pressure may be measured across multiple breaths.

At Step 912, the patient's total expiratory pressure is measured from a point in the hardware downstream of the flow source. The total expiratory pressure may be represented by PE.

At Step 920, the expiratory pressure from the patient may be calculated using the transitional pressure (calculated at Step 904) and the total expiratory pressure (calculated at Step 912). The transitional pressure may be subtracted from the total expiratory pressure to obtain the expiratory pressure from the patient. The patient expiratory pressure may be represented by PP, such that it is calculated by PP=PE−PT.

At Step 906, the cannula pressure from the cannula flow is determined. This can be done using the resistance to flow of the hardware (calculated at Step 902) and the transitional pressure (calculated at Step 904). The pressure caused by the resistance to flow of the hardware can be subtracted from the transitional pressure to obtain the pressure from cannula flow, which may be represented as PC such that PC=PT−PH.

At Step 908, the cannula flow's concentration of the gas of interest (e.g., $CO_2$) can be measured. In many cases, this concentration will be known and/or a constant and may be represented as CC. If the cannula is delivering air, then the concentration of $CO_2$ will be approximately 0.03%.

At Step 910, the concentration of the gas of interest in the cannula flow can be multiplied with the pressure from the cannula flow to determine the pressure contribution of the gas of interest in the cannula flow, which may be represented as PCC. The concentration of the gas of interest in the cannula flow could be measured in the system, assumed from literature according to the gas mixture flowing through the cannula, or assumed to be zero if concentrations are known to be negligible. The equation may be represented as PCC=CC×PC.

At Step 914, the concentration of the gas of interest in the total expiratory pressure can be measured, and may be represented as CE.

At Step 916, the pressure contribution of the gas of interest in the total expiratory pressure may be calculated by multiplying the total expiratory pressure by the measured gas of interest's concentration. The pressure contribution of the gas of interest in the total expiratory pressure may be represented as PCE, such that PCE=CE×PE.

At Step 918, the pressure contribution of the gas of interest in the expiratory pressure from the patient may be determined using the pressure contributions of the gas of interest in the total expiratory pressure and the pressure contribution of the gas of interest in the cannula flow. The pressure contributed by the gas of interest in the expiratory pressure from the patient may be represented as PCP, and it may be calculated by PCP=PCE−PCC.

At Step 922, the concentration of the exhaled gas of interest from the patient may be calculated by dividing the pressure contribution of the gas of interest in the total expiratory pressure by the expiratory pressure from the patient, and then multiplying the result by 100. The concentration of the exhaled gas of interest from the patient may be represented by CP, such that CP=(PCP/PP)×100.

An example calculation for $CO_2$ as the gas of interest using the pressure dilution technique of FIG. 9 is provided below:
1) Pressure caused by the resistance to flow of the hardware, PH=1 cmH2O
2) Transitional pressure, PT=5.2 cmH2O
3) Total expiratory pressure, PE=6.4 cmH2O
4) Determined patient expiratory pressure PP=PE−PT=1.2 cmH2O (see Note below)
5) Determined pressure from cannula flow PC=PT−PH=4.2 cmH2O (see Note below)
6) Concentration of $CO_2$ in the cannula flow CC=0.03%
7) Concentration of $CO_2$ in the total expiratory pressure CE=0.8%
8) Pressure contribution of $CO_2$ in the cannula flow PCC=CC×PC=0.001 cmH2O
9) Pressure contribution of $CO_2$ in the total expiratory pressure PCE=CE×PE=0.05 cmH2O
10) Pressure contribution of $CO_2$ in the patient expiratory pressure PCP=PCE−PCC=0.049 cmH2O (see Note)
11) Exhaled $CO_2$ concentration CP=(PCP/PP)×100=4.1%

Note: The equations used can be generalized where the entity of interest is a function of the entities used to estimate it. The subtraction equations used in the example are one type of function that could be used.

FIG. 10 illustrates how transitional pressure can be determined from a pressure waveform of a breathing cycle. The pressure waveform crosses zero at the inflection point between inspiration and expiration. The point where the pressure is zero is the transitional pressure.

GENERAL ALTERNATIVES AND CONCLUSION

In some embodiments, the phase of the breath cycle can be monitored and exhaled gas measurements can be correlated with the phase of the breath. The measurements can be displayed such that the trend of exhaled gas of interest can be displayed with a representation of the breath cycle. In some embodiments, the maximum exhaled gas of interest measurement is used as the measured exhaled gas concentration for a particular breath cycle. In some embodiments, trends over longer periods of time, such as, for example, several hours can be monitored and displayed. Trends, and particularly, longer trends of exhaled gases can indicate a patient's response to a particular treatment or a patient's response to a change in treatment.

In an embodiment where exhaled oxygen concentration is calculated, gas exchange parameters such as $O_2$ uptake and Respiratory Exchange Ratio (or Quotient) (RER=$CO_2$ output/$O_2$ uptake) can also be determined. This information is important for clinicians, and for monitoring metabolic requirements. Determining when these parameters fall outside user-defined targets or limits (for example, via notifications, alarms etc.), showing trends in these values to indicate therapy efficacy or change in patient condition are very helpful to a practitioner.

Once a desired measurement is obtained, the measurement can be displayed to the user or healthcare provider for treatment analysis purposes. The measurements can be displayed as concentrations and/or partial pressures. Trends, graphs and other visual representations of the obtained measurements can also be displayed. For example, the shape of the waveform is also useful to clinicians, so monitoring and display of the whole exhaled breath (showing the compensated gas measurement of interest) would be helpful. They can use this waveform to monitor patient condition, detect deviations from the norm and for diagnostics.

Alarm limits, thresholds, and parameters can also be based on the measurements obtained in this system. For example, an alarm parameter can trigger an alarm when a percentage of measured $CO_2$ produced rises above or below a threshold. Other alarm parameters can be set around values or trends related to $N_2O$ thresholds and $O_2$ uptake.

In some embodiments, the techniques disclosed within may be used to produce compensated values of respiratory gas concentration in order to aid in the administration of anaesthesia. In anaesthesia, pre-oxygenation is the process of administering oxygen to a patient prior to intubation, so as to extend 'the safe apnoea time'. It can also be described as de-nitrogenising the lung, as it is the nitrogen within the lungs that is displaced by a high inspired oxygen concentration. In an embodiment where exhaled nitrogen is calculated, the wash-out of nitrogen from the lungs during pre-oxygenation could be analysed. The wash-out of nitrogen may be a graph that represents the change in nitrogen concentration as nitrogen is displaced from the lungs. More details on the wash-out of nitrogen can be found in U.S. Application No. 62/140,592, filed on Mar. 31, 2015, titled "Methods, Apparatus and Systems for Pre-Oxygenation Therapy" and previously incorporated by reference.

In anaesthesia, the compensated $CO_2$ values could be used:

To determine the adequacy of ventilation, both patient and machine ventilation

For the assessment of endotracheal tube and laryngeal mask position

To determine if there has been a disconnection from a mechanical ventilator

To monitor the frequency and regularity of ventilation when a patient is under sedation For early detection of adverse respiratory events To monitor a period of apnoea and estimate its length (more details on this can be found in U.S. Application No. 62/140,633, filed Mar. 31, 2015, titled "FLOW THERAPY SYSTEM AND METHOD", and previously incorporated by reference.)

To monitor a patient and determine when a patient has transitioned into an apnoea The concentration of the gas of interest measured decreases with increasing flow rate due to flushing, making detection harder at higher flow rates. At lower flow rates, there is less flushing and it is easier to measure the gas of interest's concentration. Therefore the Optiflow cannula flow rate could be altered during expiration to provide a lower flow rate in order to sample the gas with less dilution. This idea could be extended to techniques that alter the cannula flow from a constant high flow e.g. pulse flow at the transition between expiration and inspiration, breath dependent cannula flow, oscillatory flow. When the cannula flow is not constant, the dilution techniques could be used during times when the cannula flow is at its lowest.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel techniques and systems described herein can be embodied in a variety of other forms; furthermore, various omissions, substitutions and changes in the form of the techniques and systems described herein can be made without departing from the spirit of the inventions disclosed herein. The claims and their equivalents are intended to cover such forms or modifications as would fall within the scope and spirit of certain of the inventions disclosed herein.

What is claimed is:

1. A system for estimating exhaled gas during flow respiratory therapy, the system comprising:
   a first sensor configured to measure a concentration of a gas of interest in a total expiratory flow; and
   one or more hardware computer processors in communication with the first sensor and configured to execute a plurality of computer executable instructions configured to:
   determine an exhaled concentration of the gas of interest using a patient-only contribution to an expiratory flow rate attributable to the gas of interest based at least in part on measurements from the first sensor and an instantaneous expiratory flow rate of a patient; and
   display the exhaled concentration of the gas of interest;
   wherein the system further comprises a second sensor configured to measure a parameter indicative of instantaneous expiratory flow rate of the patient, and wherein the one or more hardware computer processors are also in communication with the second sensor, and wherein the one or more hardware computer processors are further configured to execute a plurality of computer executable instructions configured to:
   determine the instantaneous expiratory flow rate of the patient, wherein the instantaneous expiratory flow rate comprises a rate of flow of gas exhaled by the patient;
   determine a delivered flow rate, wherein the delivered flow rate comprises a rate of flow of gas within a cannula; and
   determine a total expiratory flow rate using the instantaneous expiratory flow rate and the delivered flow rate, wherein the total expiratory flow rate comprises the rate of flow of gas associated with the total expiratory flow.

2. The system of claim 1, wherein the second sensor configured to measure the parameter indicative of instantaneous expiratory flow rate of the patient is at least one pressure sensor.

3. The system of claim 1, wherein the one or more hardware computer processors are further configured to execute a plurality of computer executable instructions configured to:
   determine the concentration of the gas of interest in the total expiratory flow;

determine a portion of the total expiratory flow rate attributable to the gas of interest using the total expiratory flow rate and the concentration of the gas of interest in the total expiratory flow;

determine a concentration of the gas of interest within the cannula; and determine a portion of the delivered flow rate attributable to the gas of interest using the delivered flow rate and the concentration of the gas of interest within the cannula.

4. The system of claim 3, wherein the one or more hardware computer processors are further configured to execute a plurality of computer executable instructions configured to:

determine a patient-only contribution to the expiratory flow rate attributable to the gas of interest using the portion of the total expiratory flow rate attributable to the gas of interest and the portion of the delivered flow rate attributable to the gas of interest.

5. The system of claim 3, wherein determining the portion of the total expiratory flow rate attributable to the gas of interest comprises multiplying the total expiratory flow rate by the concentration of the gas of interest in the total expiratory flow.

6. The system of claim 3, wherein determining the portion of the delivered flow rate attributable to the gas of interest comprises multiplying the delivered flow rate and the concentration of the gas of interest within the cannula.

7. The system of claim 3, wherein determining the patient-only contribution to the expiratory flow rate attributable to the gas of interest comprises subtracting the portion of the delivered flow rate attributable to the gas of interest from the portion of the total expiratory flow rate attributable to the gas of interest.

8. The system of claim 1, wherein the flow respiratory therapy is a non-sealed high flow respiratory therapy, and wherein the system further comprises an unsealed patient interface.

9. The system of claim 8, further comprising a humidifier and wherein the system is configured to deliver humidified gas to the unsealed patient interface.

10. The system of claim 8, wherein the one or more hardware computer processors are configured to determine a compensated exhaled gas measurement at least in part based on determining a concentration or volume of a gas component in a flow of gases delivered via the unsealed patient interface.

11. The system of claim 1, wherein the gas of interest is $CO_2$ and wherein the first sensor is a capnometer.

12. The system of claim 1, wherein the system is configured to deliver gas at a preset flow rate.

13. The system of claim 12, wherein the preset flow rate comprises a constant flow rate.

14. The system of claim 12, wherein the preset flow rate comprises an oscillatory flow rate.

15. The system of claim 12, wherein the system is configured to deliver gas at a flow rate of greater than 10 L/min.

16. The system of claim 1, wherein the system is configured to deliver high flow respiratory support.

17. The system of claim 16, wherein the system is configured to deliver gas at a flow rate of greater than 10 L/min.

18. The system of claim 1, wherein the system further comprises a sealed patient interface.

19. The system of claim 1, wherein the system is further configured to deliver gas at a flow rate at or above 40 L/min.

20. The system of claim 1, wherein the system is used on a patient undergoing an anaesthetic procedure.

* * * * *

UNITED STATES PATENT AND TRADEMARK OFFICE
CERTIFICATE OF CORRECTION

PATENT NO. : 12,048,527 B2
APPLICATION NO. : 16/905429
DATED : July 30, 2024
INVENTOR(S) : Alicia Jerram Hunter Evans It is certified that error appears in the above-identified patent and that said Letters Patent is hereby corrected as shown below:

In the Specification

In Column 1, Line 16, delete "which is" and insert --which--.

In Column 3, Line 14, delete "CO2" and insert --CO2.--.

In Column 3, Line 64, delete "capnometer;" and insert --capnometer.--.

In Column 5, Line 3, delete "capnometer;" and insert --capnometer.--.

In Column 5, Line 63, delete "interest;" and insert --interest.--.

In Column 8, Line 41, delete "l/min)." and insert --L/min).--.

In Column 13, Line 43, delete "canography" and insert --capnography--.

In Column 14, Lines 12-13, delete "ET $CO_2$" and insert --$ETCO_2$--.

In Column 15, Line 10, delete "connector)," and insert --connector).--.

In Column 17, Line 39, delete "$Qc,_{gas}$." and insert --$Qc,_{gas}$.--.

In Column 17, Line 47, delete "$Qp,_{gas}$." and insert --$Qp,_{gas}$.--.

In Column 18, Line 1, delete "$Qc,_{CO2}$" and insert --$Qc,_{CO2}$--.

In Column 18, Line 6, delete "5.94%" and insert --5.94%.--.

In Column 18, Line 64, delete "connector)," and insert --connector).--.

Signed and Sealed this
Tenth Day of December, 2024

Katherine Kelly Vidal
*Director of the United States Patent and Trademark Office*

CERTIFICATE OF CORRECTION (continued)
U.S. Pat. No. 12,048,527 B2

In Column 19, Line 32, delete "changing" and insert --changing.--.

In Column 22, Line 43, delete "4.96%" and insert --4.96%.--.

In Column 25, Line 29, delete "3.88%" and insert --3.88%.--.

In Column 26, Line 33, delete "[0113]The" and insert --The--.

In Column 28, Line 28, delete "4.1%" and insert --4.1%.--.

In Column 29, Line 49, delete "apnoea" and insert --apnoea.--.